US012599615B2

(12) United States Patent
Ruiz Cánovas et al.

(10) Patent No.: US 12,599,615 B2
(45) Date of Patent: Apr. 14, 2026

(54) USE OF CAROTENOIDS IN THE TREATMENT OF SENESCENCE-RELATED DISEASES

(71) Applicant: GAT THERAPEUTICS, S.L., Barcelona (ES)

(72) Inventors: Eugènia Ruiz Cánovas, Granollers (ES); Ariadna Emeric Casterà, Barcelona (ES); Xavier Álvarez Micó, Tarrasa (ES); Jaume Mercadé Roca, Barcelona (ES); Noelia Gesteira Pérez, Vigo (ES)

(73) Assignee: GAT THERAPEUTICS, S.L., Barcelona (ES)

( * ) Notice: Subject to any disclaimer, the term of this patent is extended or adjusted under 35 U.S.C. 154(b) by 953 days.

(21) Appl. No.: 17/436,225

(22) PCT Filed: Mar. 4, 2020

(86) PCT No.: PCT/EP2020/055636

§ 371 (c)(1),
(2) Date: Sep. 3, 2021

(87) PCT Pub. No.: WO2020/178309

PCT Pub. Date: Sep. 10, 2020

(65) Prior Publication Data

US 2022/0152062 A1 May 19, 2022

(30) Foreign Application Priority Data

Mar. 5, 2019 (EP) .................................... 19382166

(51) Int. Cl.

| | |
|---|---|
| ***A61K 31/635*** | (2006.01) |
| ***A23L 33/00*** | (2016.01) |
| ***A23L 33/10*** | (2016.01) |
| ***A61K 8/34*** | (2006.01) |
| ***A61K 8/35*** | (2006.01) |
| ***A61K 8/49*** | (2006.01) |
| ***A61K 31/047*** | (2006.01) |
| ***A61K 31/122*** | (2006.01) |
| ***A61K 31/336*** | (2006.01) |
| ***A61P 35/00*** | (2006.01) |
| ***A61P 39/00*** | (2006.01) |
| ***A61Q 19/08*** | (2006.01) |

(52) U.S. Cl.

CPC ............ *A61K 31/635* (2013.01); *A23L 33/10* (2016.08); *A23L 33/40* (2016.08); *A61K 8/345* (2013.01); *A61K 8/35* (2013.01); *A61K 8/494* (2013.01); *A61K 8/4973* (2013.01); *A61K 31/047* (2013.01); *A61K 31/122* (2013.01); *A61K 31/336* (2013.01); *A61P 35/00* (2018.01); *A61P 39/00* (2018.01); *A61Q 19/08* (2013.01); *A23V 2002/00* (2013.01)

(58) Field of Classification Search

CPC .................................................... A61K 31/635

See application file for complete search history.

(56) References Cited

U.S. PATENT DOCUMENTS

| | | | |
|---|---|---|---|
| 8,546,399 B2 | 10/2013 | Bruncko et al. |
| 2011/0070258 A1 | 3/2011 | Jimenez Del Ro et al. |
| 2014/0005190 A1 | 1/2014 | Baell et al. |
| 2016/0339019 A1 | 11/2016 | Laberge et al. |
| 2017/0224680 A2 | 8/2017 | Laberge et al. |

FOREIGN PATENT DOCUMENTS

| | | |
|---|---|---|
| EP | 3231421 | 10/2017 |
| EP | 3247375 B1 | 8/2021 |
| WO | 2013090645 A1 | 6/2013 |
| WO | 2015116740 A1 | 8/2015 |
| WO | 2018025944 A1 | 2/2018 |

OTHER PUBLICATIONS

Heike Fuhrmann-Stroissnigg et al., "Identification of HSP90 inhibitors as a novel class of senolytics," Nature Communications, Sep. 4, 2017, vol. 8, No. 1.

Guoping Zhao et al., "Activation of the Proapoptotic Bcl-2 Protein Bax by a Small Molecule Induces Tumor Cell Apoptosis," Mol Cell Biol., Apr. 2014, pp. 1198-1207, vol. 34, No. 7.

Goberdhan P. Dimri, et al., "A biomarker that identifies senescent human cells in culture and in aging skin in vivo," Proc. Natl. Acad. Sci. USA, Sep. 1995, pp. 9363-9367, vol. 92.

Jean-Philippe Coppe et al., "Senescence-Associated Secretory Phenotypes Reveal Cell-Nonautonomous Functions of Oncogenic RAS and the p53 Tumor Suppressor," PLoS Biol, Dec. 2008, pp. 2853-2868, vol. 6, issue 12.

Ryan R. Gordon et al., "Cellular Senescence and Cancer Chemotherapy Resistance," Drug Resist Updat., Feb. 2012, pp. 123-131, vol. 15.

Marco Demaria, "Senescent cells: New target for an old treatment?," Mol. Cell Oncol., Feb. 2017, vol. 4, No. 3.

Amirreza Zarekarizi et al., "Approaches for the sustainable production of fucoxanthin, a xanthophyll with potential health benefits," Journal of applied phycology, Jun. 29, 2018, pp. 281-299, vol. 31.

Jihane Gasmi et al., "Growth Inhibitory, Antiandrogenic, and Proapoptotic Effects of Punicic Acid in LNCaP Human Prostate Cancer Cells," Journal of Agricultural and Food Chemistry, Dec. 2010, pp. 12149-12156, vol. 58, No. 23.

Masashi Hosokawa et al., "Fucoxanthin induces apoptosis and enhances the antiproliferative effect of the PPARgamma ligand, troglitazone, on colon cancer cells," Biochimica et Biophysica acta, Nov. 18, 2004,pp. 113-119, vol. 1675, No. 1-3.

(Continued)

*Primary Examiner* — Brian E Mcdowell

(74) *Attorney, Agent, or Firm* — Pilloff Passino & Cosenza LLP; Rachel K. Pilloff; Sean A. Passino

(57) ABSTRACT

The invention relates to a combination comprising a carotenoid, a carotenoid metabolite, a carotenoid derivative, analogue or an ester or salt thereof and a second component selected from the group consisting of an inhibitor of one or more members of the BCL-2 anti-apoptotic protein family, an activator of pro-apoptotic BCL-2 family members, a senolytic agent and a senomorphic agent. The invention also relates to a food, a cosmeceutical, a nutraceutical, a cosmetic or pharmaceutical composition comprising the combination of the invention and its use in a cosmetic method and it medical uses.

8 Claims, 4 Drawing Sheets

(56) References Cited

OTHER PUBLICATIONS

Mei Ming et al., "Effect of ligand troglitazone on peroxisome proliferator-activated receptor gamma expression and cellular growth in human colon cancer cells," World J Gastroenterol, Dec. 7, 2006, pp. 7263-7270, vol. 12.

Yixiang Liu et al., "Protective Effect of Fucoxanthin Isolated from Laminaria japonica against Visible Light-Induced Retinal Damgage Both in Vitro and in Vivo," Journal of Agricultural and Food Chemistry, Jan. 4, 2016, pp. 416-424, vol. 64, No. 2.

Akira Asai et al., "Biotransformation of fucoxanthinol into amarouciaxanthin A in mice and HepG2 cells: formation and cytotoxicity of fucoxanthin metabolites," Drug metabolism and disposition, Jan. 1, 2004, pp. 205-211, vol. 32, No. 2.

Tadeusz Robak, "BCL-2 inhibitors for Chronic Lymphocytic Leukemia," Journal of Leukemia, Jan. 1, 2015, vol. 3, issue 3.

Marissa J. Schafer, "Targeting Senescent Cells in Fibrosis: Pathology, Paradox, and Practical Considerations," Curr Rheumatol Rep, Jan. 26, 2018, vol. 20, No. 3.

A.V. Borodkina et al., "Social Life" of Senescent Cells: What Is SASP and Why Study It?, Acta Naturae, Feb. 2018, vol. 10, No. 1.

Dominick G.A. Burton et al., "Obesity and type-2 diabetes as inducers of premature cellular senescence and ageing," Biogerontology, Jul. 2018, pp. 447-459, vol. 19.

Marco Demaria et al., "Cellular senescence promotes adverse effects of chemotherapy and cancer relapse," Cancer Discovery, Dec. 2016, pp. 165-176.

Alexey Moskalev et al., "Transcriptome analysis reveals mechanisms of geroprotective effects of fucoxanthin in *Drosophila*," BMC Genomics, Jan. 2018, 19(Suppl 3):77.

Cynthia J. Sieben et al., "Two-Step Senescence-Focused Cancer Therapies," Trends in Cell Biology, May 2018, pp. 723-737.

Po-Ming Chang et al., "Fucoidan-Fucoxanthin Ameliorated Cardiac Function via IRS1/GRB2/ SOS1, GSK3β/CREB Pathways and Metabolic Pathways in Senescent Mice," Marine Drugs, Jan. 2019, vol. 17.

International Search Report and Written Opinion for PCT/EP2020/055636, mailed Jul. 20, 2020.

Yue Yang et al., "Astaxanthin, a xanthophyll carotenoid, inhibited and reversed the activation of mouse primary hepatic stellate cells via the modulation of histone deacetylases {39.1)," The FASEB Journal, Apr. 2014.

Extended European Search Report for EP Application No. 23166682.7, mailed Jul. 5, 2023.

Xiaoming Gong, et al, "Carotenoid Lutein Selectively Inhibits Breast Cancer Cell Growth and Potentiates the Effect of Chemotherapeutic Agents through ROSMediated Mechanisms", Molecules, vol. 23, No. 4:905, pp. 1-18, Apr. 14, 2018 (Apr. 14, 2018), XP093011326, ISSN: 1433-1373, 001: DOI: 10.3390/molecules23040905.

Leonel Pereira, "Seaweeds as Source of Bioactive Substances and Skin Care Therapy-Cosmeceuticals, Algotheraphy, and Thalassotherapy", Cosmetics, vol. 5, No. 4, 68, Nov. 22, 2018 (Nov. 22, 2018), pp. 1-41 DOI:10.3390/cosmetics5040068.

European search report (EESR) issued Apr. 17, 2023 by the European Patent Office in relation to the application EP22191374.2.

Itaru Urikura, et al., "Protective Effect of Fucoxanthin against UVB-Induced Skin Photoaging in Hairless Mice", Bioscience, Biotechnology, and Biochemistry, vol. 75, Issue 4, Apr. 23, 2011, pp. 757-760, DOI:10.1271/bbb.110040.

Hartmut Geiger, "Depleting senescent cells to combat aging," Nature Medicine, Jan. 2016, pp. 23-24, vol. 22, No. 1. PMID: 26735406, DOI: 10.1038/nm.4024.

Jianhui Chang et al., "Clearance of senescent cells by ABT263 rejuvenates aged hematopoietic stem cells in mice," Nature Medicine, Jan. 2016, pp. 78-86, vol. 22, No. 1; epublished Dec. 14, 2015. PMID: 26657143, PMCID: PMC4762215, DOI: 10.1038/nm.4010.

Scheme 1

Scheme 2

USE OF CAROTENOIDS IN THE TREATMENT OF SENESCENCE-RELATED DISEASES

FIELD OF THE INVENTION

The present invention is in the field of medicine. More specifically, it is in the field of the treatment of diseases or conditions wherein the removal of senescent cells is beneficial.

BACKGROUND OF THE INVENTION

Cellular senescence is characterized by an irreversible loss of proliferative potential, as well as specific changes in cell morphology and gene expression that ultimately lead to impaired cell function.

Given that senescent cells have been causally implicated in certain aspects of age-related decline in health and may contribute to certain diseases, and are also induced as a result of necessary life-preserving chemotherapeutic and radiation treatments, the presence of senescent cells may have deleterious effects to millions of patients worldwide.

Document US2016339019 discloses inhibitors of BCL-2 anti-apoptotic protein family and document EP3247375A2 discloses inhibitors of SYK and inhibitors of ASK1 as agents suitable for removing senescent cells in humans.

There is still a need in the state of the art to provide new and existing compounds that therapeutically target senescent cells and that can be used in the treatment of diseases associated with cellular senescence.

SUMMARY OF THE INVENTION

The authors of the present invention have found that carotenoids act synergistically with inhibitors of BLC2 anti-apoptotic family members, activators of BCL-2 pro-apoptotic family members, senolytic agents and senomorphic agents in reducing senescence and in cancer therapy.

Thus, in a first aspect the invention relates to a combination comprising a carotenoid, a carotenoid metabolite, a carotenoid derivative, analogue or an ester or salt thereof and a second component selected from the group consisting of an inhibitor of one or more members of the BCL-2 anti-apoptotic protein family, an activator of BCL-2 pro-apoptotic family members, a senolytic agent and a senomorphic agent.

In second aspect, the invention relates to a food, cosmeceutical, nutraceutical, cosmetic or pharmaceutical composition comprising the combination of the invention.

In a third aspect, the invention relates to a cosmetic method for preventing and/or decreasing cutaneous senescence and/or for ameliorating the cosmetic adverse effects of aging comprising administering the combination according to any of claims 1 to 4 or the food, cosmeceutical, nutraceutical or cosmetic composition according to claim 5 to a subject in need thereof.

In a fourth aspect, the invention relates to the combination of the invention or pharmaceutical composition according to the invention for use in medicine.

In a fifth aspect, the invention relates to the combination according to the invention or the pharmaceutical composition according to the invention for use in the treatment of cancer.

In a sixth aspect, the invention relates to the combination according to the invention or the pharmaceutical composition according to the invention for use in the treatment of a senescence-associated disease or disorder.

In a seventh aspect, the invention relates to the combination according to the invention or the food, nutraceutical or pharmaceutical composition according to the invention for use in enhancing the effectiveness of an antitumoral compound.

In an eighth aspect, the invention relates to a carotenoid, carotenoid metabolite, carotenoid derivative, analogue or an ester or salt thereof for use in the treatment of a senescence-associated disease or disorder.

In a ninth aspect, the invention relates to a carotenoid, a carotenoid metabolite, carotenoid derivative, analogue or an ester or salt thereof for use in enhancing the effectiveness of an antitumoral compound.

In a tenth aspect, the invention relates to a carotenoid, a carotenoid metabolite, carotenoid derivative, analogue or an ester or salt thereof for use in reducing the adverse effect of an antitumoral treatment.

DETAILED DESCRIPTION OF THE INVENTION

Combination

Figure 1:
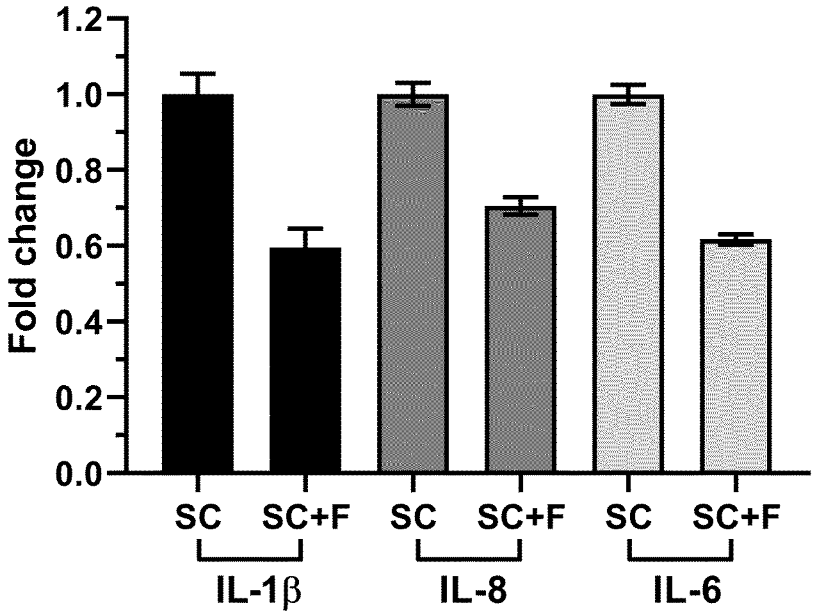
FIG. 1. ILs secretion by SK-Mel-103 cells upon treatment with palbociclib. Error bars indicate the standard deviation from 3 technical replicates. SC, senescent cells; F, fucoxanthin.

The authors of the present invention have found that carotenoids and Bcl-2 inhibitors show a synergistic cytotoxic effect in certain cancer lines. Accordingly, in a first aspect, the invention relates to combination comprising a carotenoid, a carotenoid metabolite, a carotenoid derivative, analogue or an ester or salt thereof and a second component selected from the group consisting of an inhibitor of one or more members of the BCL-2 anti-apoptotic protein family, an activator of BCL-2 pro-apoptotic family members, a senolytic agent and a senomorphic agent.

"Combination" or "composition", as used herein, indicates that the carotenoid, carotenoid metabolite, carotenoid derivative, analogue or an ester or salt thereof and the one or more members of the BCL-2 anti-apoptotic protein family, an activator of BCL-2 pro-apoptotic family members, a senolytic agent and a senomorphic agent can be formulated in the same medicine formulation or they can also be formulated in different ones, but different medicine formulation shall be included in the same drug through combined package and be used at the same time, in sequence or in turn.

The term "carotenoid", as used herein, refers to a group of naturally-occurring pigments produced mainly by plants, yeast and algae, which have a common polyisoprenoid-based structure, a long polyene chain forming the chromophore and near symmetry around the central double bond. Tail-to tail linkage of two $C_{20}$ geranylgeranyl diphosphate molecules produces the parent $C_{40}$ carbon skeleton. The polyene chain may also have a cyclyl group at one or both ends of the molecule.

Carotenoids are divided into two classes, xanthophylls (which contain oxygen atoms) and carotenes (which contain no oxygen atoms).

In a preferred embodiment, the carotenoid of the invention is a xanthophyll. In a more preferred embodiment the xanthophyll is selected from the group consisting of α-cryptoxanthin, β-cryptoxanthin, adonirubin, adonixanthin, alloxanthin, amarouciaxanthin (in particular amarouciaxanthin A), antheraxanthin, astaxanthin, auroxanthin, caloxanthin, cantaxanthin, capsanthin, capsanthin-5-6-epoxide, capsorubin, crocoxanthin, diadinoxanthin, diatoxanthin, echinenone, fucoxanthin, fucoxanthinol, iso-fucoxanthin, iso-fucoxanthinol, lutein, luteoxanthin, mutatoxanthin, neoxanthin, nostoxanthin, violaxanthin, zeaxanthin and combinations or derivatives thereof. More preferably, the xanthophyll is selected from amarouciaxanthin A, capsanthin, fucoxanthin, fucoxanthinol, neoxanthin, lutein, zeaxanthin and combinations thereof. More preferably, the xanthophyll is selected from amarouciaxanthin A, fucoxanthin, fucoxanthinol, neoxanthin, lutein and combinations thereof. Still more preferably, the xanthophyll is selected from amarouciaxanthin A, fucoxanthin, fucoxanthinol, neoxanthin and combinations thereof. Still more preferably, the xanthophyll is selected from amarouciaxanthin A, fucoxanthin, fucoxanthinol and combinations thereof. Even more preferably the xanthophyll is fucoxanthin or amarouciaxanthin A.

In one embodiment, the xanthophylls described above refer to the all-trans forms thereof.

In another preferred embodiment, the carotenoid is fucoxanthin. In another preferred embodiment, the carotenoid is fucoxanthinol. In another preferred embodiment, the carotenoid is amarouciaxanthin. In a more preferred embodiment the carotenoid is amarouciaxanthin A. In another preferred embodiment, the carotenoid is neoxanthin. In another preferred embodiment, the carotenoid is astaxanthin. In another preferred embodiment, the carotenoid is zeaxanthin. In another preferred embodiment, the carotenoid is lutein.

The carotenoid of the invention can be provided from an algal, fungal or plant extract. When the carotenoid, such as the above mentioned xanthophylls used in the invention, comes from a plant extract or alga extract, the product is obtained by an extractive process on any of the organisms or plants, either by soaking said organisms or plants with a solvent or by extraction with more sophisticated techniques involving the use of pressure or supercritical fluids.

Examples of suitable algae for the provision of carotenoids in the combination of the invention, include microalgae from the phylums Cyanophyta, Chlorophyta, Rhodophyta, Heterokontophyta, and Haptophyta. The algae can be a green microalga such as Chlorella, Scenedesmus, Dunialiella (for beta-carotene), Haematococcus (for astaxanthin) and Bracteacoccus; haptophyte microalgae such as Isochrysis (for fucoxanthin and lutein); and heterokontophyta microalgae such as Phaeodactylum, Ochromonas and Odontella. Examples of suitable macroalgae comprise all brown algae, and in particular *Fucus vesiculosus, Fucus evanescens, Laminaria* sp., and Sargassum sp. (all for fucoxanthin). Certain fungi are known to produce xantophylls, such as Xanthophyllomyces dendrorhous. In addition, carotenoids can also be obtained from animal sources such as egg yolk. Plants and plant parts suitable for the production of carotenoids, such as the xanthophylls used in the invention, include, without limitation, marigold flowers, maize, kiwi, red seedless grapes, zucchini, pumpkin, spinach, orange pepper, yellow squash, cucumber, pea, green pepper, red grape, butternut, orange, honeydew, celery, green grapes, Brussels sprouts, scallions, green beans, broccoli, apple, mango, green lettuce, tomato, peach, yellow pepper, nectarine, red pepper, carrots, cantaloupe, apricots, bell peppers and green kidney beans.

"Carotenoid metabolite" as used herein relates to a carotenoid modified by, for example, hydrogenation, dehydrogenation, double-bond migration, chain shortening or extension, rearrangement, isomerization, oxidation or combinations of these processes under different conditions. Apart from these, carotenoid metabolites may also form due to the presence of enzymes monooxygenase, cycloxygenase and dioxygenase.

Examples of β-carotene metabolites are retinol, retinal and retinoic acid, β-ionone, β-apo-l4'-carotenal, β-apo-10'-carotenal, β-apo-8'-carotenal and -carotene 5,8-endoperoxide-2,3-dihydro-β-apocarotene-13-one, 5,6-monoepoxide, retinoyl β-D-glucuronide, β-apo-12'-carotenoic acid, β-apo-14'-carotenoic acid, β-apo-14'-carotenal, β-apo-14'-carotenoic acid, and β-apo-13-carotenone.

Lycopene metabolites are, for example, acyclo retinoic acid, 2,7,11-trimethyl-tetradecahexaene-1,14-dial, (E,E,E)-4-methyl-8-oxo-2,4,6-nonatrienal (MON), apo-6-, apo-8'-, apo-10'-, apo-12'- and apo-14'-lycopenal and apo-10'-lycopenoic acid. Examples of lutein metabolites are 3'-epilutein, 3'-oxolutein, 3'-dehydrolutein, meso-zeaxanthin, methoxy-zeaxanthin, oxime derivatives of 3-hydroxy-β-ionone and 3-hydroxy-14-apocarotenal, 3-hydroxy-3', 4'-didehydro-β,γ-carotene and 3-hydroxy-2',3'-didehydro-β,ε-carotene Astaxanthin metabolites are for example 3-hydroxy-4-oxo-β-ionone and 3-hydroxy-4-oxo-7,8-dihydro-β-ionone. An example of canthaxanthin metabolite is 4-oxoretinoic acid "Derivatives of carotenoids" are also included in the context of the present invention. In a particular embodiment, said derivatives include xantophylls and carotenes containing one or more cis double bond, including, without limitation, 9 cis derivatives, 9' cis derivatives, 13 cis derivatives, 13' cis derivatives, 15 cis derivatives, 15' cis derivatives and any combination thereof.

In another embodiment, synthetic derivatives wherein xantophylls and carotenes are used as starting scaffolds for said carotenoid derivatives are used. In some embodiments, the carotenoid derivatives include compounds having a structure including a polyene chain (i.e., backbone of the molecule). Said polyene chain may include between about 5 and about 15 unsaturated bonds, more particularly 7 or more conjugated double bonds.

The combination of the invention may also comprise carotenoid analogs. As used herein the terms "carotenoid analogs" may be generally defined as carotenoids and the biologically active structural analogs thereof. Typical analogs include molecules which demonstrate equivalent or improved biologically useful and relevant function, but which differ structurally from the parent compounds. Parent carotenoids are selected from more than 600 naturally-occurring carotenoids described in the literature, and their stereo- and geometric isomers. Such analogs may include but are not limited to, esters, ethers, carbonates, amides, carbamates, phosphate esters and ethers, sulfates, glycoside ethers, with or without spacers (linkers).

The combination of the invention may also comprise an ester of the carotenoid, (e.g., acetate, formate, and benzoate derivatives)

The combination of the invention may also comprise a salt of a carotenoid, carotenoid metabolite, carotenoid derivative or carotenoid analogue. The term “salt” is to be understood as meaning any form of the active compound according to the invention in which this assumes an ionic form or is charged and is coupled with a counter-ion (a cation or anion) or is in solution. By this are also to be understood complexes of the active compound with other molecules and ions, in particular complexes which are complexed via ionic interactions. The definition includes in particular physiologically acceptable salts; this term must be understood as equivalent to “pharmacologically acceptable salts” or “pharmaceutically acceptable salts”.

According to the invention, the second component is selected from the group consisting of a senolytic agent, a senomorphic agent, an inhibitor of one or more member of the BCL-2 anti-apoptotic protein family and an activator of BCL-2 pro-apoptotic family members. In the present invention, the second component is not troglitazone and/or punicic acid.

“Senolytic agent”, as used herein relates to a compound that (preferentially or to a greater degree) destroys, kills, removes, or facilitates selective destruction of senescent cells. In other words, the senolytic agent destroys or kills a senescent cell in a biologically, clinically, and/or statistically significant manner compared with its capability to destroy or kill a non-senescent cell. A senolytic agent is used in an amount and for a time sufficient that selectively kills established senescent cells but is insufficient to kill (destroy, cause the death of) a non-senescent cell in a clinically significant or biologically significant manner. In certain embodiments, the senolytic agents described herein alter at least one signaling pathway in a manner that induces (initiates, stimulates, triggers, activates, promotes) and results in (i.e., causes, leads to) death of the senescent cell. The senolytic agent may alter, for example, either or both of a cell survival signaling pathway (e.g., Akt pathway) or an inflammatory pathway, for example, by antagonizing a protein within the cell survival and/or inflammatory pathway in a senescent cell. The senolytic agent is capable of perform its function by inducing (activating, stimulating, removing inhibition of) an apoptotic pathway that leads to cell death.

A person skilled in the art knows methods for identifying and selecting senolytic agents, for example by determining the reduction of senescent cells by an agent. The level of senescent cells may be determined according to any of the in vitro assays or techniques known in the art. For example, senescent cells may be detected by morphology (as viewed by microscopy, for example); production of senescence associated markers such as, senescence-associated β-galactosidase (SA-β-gal), p16INK4a, p21, PAI-I, or any one or more SASP factors (e.g., IL-6, MMP3). Therefore a person skilled in the art will readily appreciate that characterizing an agent as a senolytic agent and determining the level of killing by an agent can be accomplished by comparing the activity of a test agent with appropriate negative controls (e.g., vehicle or diluent only and/or a composition or compound known in the art not to kill senescent cells) and appropriate positive controls. In vitro cell-based assays for characterizing senolytic agents also include controls for determining the effect of the agent on non-senescent cells (e.g., quiescent cells or proliferating cells). A senolytic agent reduces (ie., decreases) percent survival of a plurality of senescent cells (ie., in some manner reduces the quantity of viable senescent cells in the animal or in the cell-based assay) compared with one or more negative controls.

In certain embodiments, a senolytic agent may be a polypeptide, peptide, antibody, antigen-binding fragment (i.e., peptides and polypeptides comprising at least one complementary determining region (CDR)), peptibody, recombinant viral vector, or a nucleic acid. In certain embodiments, a senolytic agent is an antisense oligonucleotide, SIRNA, shRNA, or a peptide. In a particular embodiment, the polynucleotide or oligonucleotide (e.g., including a shRNA) may be delivered by a recombinant vector in which the polynucleotide or oligonucleotide of interest has been incorporated. In another preferred embodiment, the senolytic agent is a polyclonal or monoclonal antibody.

In a preferred embodiment, the senolytic agent is selected from the group consisting of Nutlin-3a, RG-7112, ABT-263 (navitoclax), ABT-199 (venetoclax), ABT-737, WEHI-539 A-1155463, MK-2206. In a more preferred embodiment, the senolytic agent is selected from the group consisting of navitoclax and venetoclax. In a more preferred embodiment, the senolytic agent is navitoclax. In another preferred embodiment, the senolytic agent is venetoclax.

In another preferred embodiment, the senolytic agent is a flavonoid.

“Flavonoid”, as used herein relates to a compound having the general structure of a 15-carbon skeleton, which consists of two phenyl rings (A and B) and a heterocyclic ring (C). This carbon structure can be abbreviated C6-C3-C6.

In a more preferred embodiment, the flavonoid is selected from the group consisting of fisetin, curcumin, alvocidib and quercetin.

In another preferred embodiment, the combination of the invention may comprise a senomorphic agent.

A “senomorphic agent”, as used herein relates to a small molecule that suppress senescent phenotypes without cell killing.

In a preferred embodiment, the senomorphic agent is selected from the group consisting of rapamycin, fluspirilene, cycloheximide, NVP-BEZ235, Loperamide, Timosaponin A-III, iguldipine and nordihydroguaiaretic acid.

Screening methods to identify senomophic agents and to differentiate from senolytic agents are known in the art, as a way of illustrative example in Fuhrmann-Stroissnigg H. et al., Nat Commun. 2017 Sep. 4;8 (1): 422.

In another preferred embodiment, the combination of the invention may comprise an inhibitor of the BCL-2 anti-apoptotic family of proteins. In the present invention, said inhibitor is not troglitazone and/or punicic acid.

“Inhibitor of one or more members of the BCL-2 anti-apoptotic protein family” relates to an inhibitor of class of key regulators of caspase activation consisting of anti-apoptotic (pro-survival) proteins having BHI-BH4 domains (BCL-2 (i.e., the BCL-2 protein member of the BCL-2 anti-apoptotic protein family), BCL-XL, BCL-w, AI, MCL-I, and BCL-B).

In certain embodiments, a BCL2 inhibitor is a selective inhibitor, meaning, that it preferentially binds to a BCL2 family member (e.g., BCL-2, MCL-1, BCL-w, BCL-b, and BFL-1/A1) over other proteins.

Methods for measuring binding affinity of an inhibitor for BCL-2 family proteins are known in the art. By way of example, binding affinity of an inhibitor may be determined using a competition fluorescence polarization assay in which a fluorescent BAK BH3 domain peptide is incubated with BCL-XL protein (or other BCL-2 family protein) in the presence or absence of increasing concentrations of the inhibitor as previously described for example in U.S. Patent Publication 20140005190.

In addition, any method known in the art can be used to determine whether a compound is a BCL2 inhibitor, illustrative and non-limitative by determining the ability to inhibit the anti-apoptotic effect, for example performing an MTT assay, Annexin V binding assays, caspase activity assays, mitochondrial membrane potential assays or analyzing DNA fragmentation and morphology.

In certain embodiment, the BCL2 inhibitor of one or more members of the BCL-2 anti-apoptotic protein family is a small molecule, a polypeptide, peptide, antibody antigen-binding fragment (i.e., peptides and polypeptides comprising at least one complementary determining region (CDR)), peptibody, recombinant viral vector, or a nucleic acid. In certain embodiments, the BCL2 inhibitor is an antisense oligonucleotide, siRNA, shRNA, or a peptide. By way of example and in certain embodiments, a BCL-XL selective peptide inhibitor is a BH3 peptide mimetic. In another preferred embodiment, the BCL2 inhibitor is a polynucleotide or oligonucleotide that specifically hybridizes to a portion of mRNA that encodes a target protein (e.g. BCL-2, MCL-1, BCL-w, BCL-b, and BFL-1/A1, BCL-x). Antisense polynucleotides bind in a sequence-specific manner to nucleic acids such as mRNA or DNA. Identification of oligonucleotides and ribozymes for use as antisense agents and identification of DNA encoding the target gene for targeted delivery involve methods well known in the art. For example, the desirable properties, lengths, and other characteristics of such oligonucleotides are well known.

In a preferred embodiment, the BCL2 inhibitor is selected from the group consisting of a compound of formula (I), Disarib, S55746, A1331852, WEHI-S39, Obatoclax, TW-37, AT101, Sabutoclax, A1210477, Umi-77, BTSA1, BAM7, MIM1, AMG-176, MIK665 (S64315), APG-1252, BXI-61 and BXI-72.

Compounds of formula (I) and their synthesis have been described in U.S. Pat. No. 8,546,399 B2. Compounds of formula (I) and have the structure depicted below:

(I)

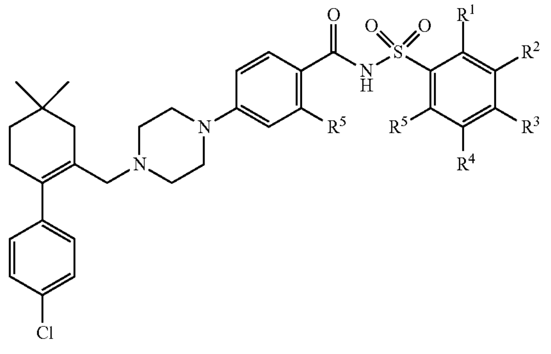

wherein $R^1$ is H;

$R^2$ is selected from the group consisting of $NO_2$, $SO_2R^7$, H, CN, F, Cl, Br, I, $CF_3$, $R^7$, $OR^7$, $SR^7$ and $C(O)NH_2$;

$R^3$ is selected from the group consisting of $NHR^8$, NHC(O)$R^8$, $OR^8$, $R^8$, F, Br, I, and Cl;

$R^4$ and $R^5$ are independently selected form the group consisting of H, F, Br, I and Cl;

$R^6$ is selected from the group consisting of H, $OR^9$, $R^9$, $SR^9$, S(O)$R^9$, $SO_2R^9$, C(O)$R^9$, CO(O)$R^9$, OC(O)$R^9$, $NHR^9$, $N(R^9)_2$, NHC(O)$R^9$, $NR^9C(O)R^9$, $NHSO_2R^9$, $NR^9SO_2R^9$, NHC(O)$OR^9$, and $NR^9C(O)OR^9$;

$R^7$ is a linear or branched $C_1$-$C_6$ alkyl optionally substituted with one or more substituents independently selected from F, Cl, Br and I;

$R^8$ is a linear or branched $C_1$-$C_6$ alkyl optionally substituted with one or more substituents selected from the group consisting of $SR^{10}$, $OR^{10}$, and $R^{10}$, and 5- to 10-membered monocyclic or bicyclic heterocyclyl containing one or more heteroatoms selected from the group consisting of N, O and S;

$R^9$ is selected from the group consisting of 5- to 10-membered monocyclic or bicyclic heteroaryl containing one or more heteroatoms selected from the group consisting of N, O and S;

$R^{10}$ is $C_6$-$C_{10}$ monocyclic or bicyclic aryl, or a pharmaceutically acceptable salt thereof.

In a particular embodiment, in the compound of formula (I) $R^1$ is H.

In another particular embodiment, in the compound of formula (I) $R^2$ is selected from the group consisting of $NO_2$, $SO_2R^7$, wherein $R^7$ is a linear or branched $C_1$-$C_3$ alkyl optionally substituted with one or more F atoms.

In another particular embodiment, in the compound of formula (I) $R^3$ is $NHR^8$ wherein $R^8$ is a linear or branched $C_1$-$C_6$ alkyl optionally substituted with one or more substituents selected from the group consisting of —S-phenyl, and 5- to 6-membered monocyclic heterocyclyl containing one or two heteroatoms selected from the group consisting of N and O; preferably $C_1$-$C_6$ alkyl optionally substituted with one or more substituents selected from the group consisting of —S-phenyl, morpholinyl and tetrahydropyranyl.

In another particular embodiment, in the compound of formula (I) $R^4$ is H.

In another particular embodiment, in the compound of formula (I) $R^5$ is H.

In another particular embodiment, in the compound of formula (I) $R^6$ is selected from the group consisting of H and $OR^9$, wherein $R^9$ is selected from the group consisting of 8- to 10-membered bicyclic heteroaryl containing one or more nitrogen atoms; preferably H and $OR^9$ wherein $R^9$ is pyrrolopyridinyl; more preferably H and $OR^9$ wherein $R^9$ is 7-azaindole.

In another particular embodiment, in the compound of formula (I) $R^8$ is a linear or branched $C_1$-$C_6$ alkyl optionally substituted with one or more substituents selected from the group consisting of —S-phenyl, and 5- to 6-membered monocyclic heterocyclyl containing one or two heteroatoms selected from the group consisting of N and O (preferably morpholinyl or tetrahydropyranyl).

In a particular embodiment, in the compound of formula (I) $R^1$, $R^4$ and $R^5$ are H; $R^2$ is selected from the group consisting of $NO_2$, $SO_2R^7$; $R^3$ is $NHR^8$; $R^6$ is selected from the group consisting of H and $OR^9$; $R^7$ is a linear or branched $C_1$-$C_3$ alkyl optionally substituted with one or more F atoms; $R^8$ is a linear or branched $C_1$-$C_6$ alkyl optionally substituted with one or more substituents selected from the group consisting of —S-phenyl, and 5- to 6-membered monocyclic heterocyclyl containing one or two heteroatoms selected from the group consisting of N and O (preferably morpholinyl or tetrahydropyranyl); and $R^9$ is selected from the group consisting of 8- to 10-membered bicyclic heteroaryl containing one or more nitrogen atoms; or a pharmaceutically acceptable salt thereof (preferably pyrrolopyridinyl, more preferably 7-azaindole); or a pharmaceutically acceptable salt thereof.

As used herein, some of the atoms, radicals, chains or cycles present in the general structures of the invention are "optionally substituted". This means that these atoms, radicals, chains or cycles can be either unsubstituted or substituted in any position by one or more, for example 1, 2, 3 or 4 substituents, 1, 2 or 3 substituents, or 1 or 2 substituents, whereby the hydrogen atoms bound to the unsubstituted atoms, radicals, chains or cycles are replaced by a substituent as indicated. When two or more substituents are present, each substituent may be the same or different.

"Alkyl" groups may be branched or unbranched, and preferably have from 1 to 6 carbon atoms. One more preferred class of alkyl groups has from 1 to 4 carbon atoms or 1 to 3 carbon atoms. Examples of alkyl groups include methyl, ethyl, n-propyl, isopropyl, n-butyl, iso-butyl, sec-butyl, tert-butyl, n-pentyl, sec-pentyl, 2-methylbutyl, 3-methylbutyl, 2,2-dimethylpropyl, pentan-3-yl, and n-hexyl.

"Heterocyclyl" as used herein, refers to a 5- to 10-membered monocyclic or bicyclic ring system containing one or more heteroatoms, for example 1, 2 or 3 heteroatoms, preferably 1 or 2 heteroatoms, selected from the group consisting of N, O and S. In bicyclic ring systems, the heteroatoms may be in one or in both rings forming the heterocyclyl ring system. Examples of heterocyclyl rings are morpholinyl, tetrahydropyranyl, piperidinyl, thiomorpholinyl, tetrahydrofuranyl, and piperazinyl. Preferably, the heterocyclyl ring has is fully saturated. Preferably the heterocyclyl ring is a 5- to 6-membered monocyclic ring containing 1 or 2 heteroatoms selected from N and O.

"Heteroaryl" as used herein, refers to an aromatic 5- to 10-membered monocyclic or bicyclic ring system containing one or more heteroatoms, for example 1, 2 or 3 heteroatoms, preferably 1 or 2 heteroatoms, selected from the group consisting of N, O and S. In bicyclic ring systems, the heteroatoms may be in one or in both rings forming the heteroaryl ring system. Examples of heteroaryl rings are pyrrolopyridinyl, quinolinyl, isoquinolinyl, quinazolinyl, quinoxalinyl, phthalazinyl, cinnolinyl, benzimidazolyl, benzofuranyl, benzofurazanyl, benzothiophenyl, benzothiazolyl, benzoxazolyl, naphthyridinyl, pyridyl, pyrazinyl, pyrazolyl, pyrimidinyl, furyl, pyrrolyl, thienyl, thiazolyl, isothiazolyl, triazolyl, tetrazolyl, isoxazolyl, oxazolyl, imidazolyl, indolyl, isoindolyl, indazolyl, indolizinyl, oxadiazolyl, thiadiazolyl, pyridazinyl, and triazinyl. Preferably, the heteroaryl ring is a 8- to 10-membered bicyclic ring containing 1 or 2 heteroatoms, preferably 1 or 2 nitrogen atoms in the ring.

"Aryl" as used herein, refers to an aromatic 6 monocyclic or bicyclic ring system consisting of hydrogen and 6 to 10 carbon atoms. Examples of aryl rings are phenyl, and naphthyl, preferably phenyl.

The term "pharmaceutically acceptable salts" refers to any salt, which, upon administration to the recipient is capable of providing (directly or indirectly) a compound as described herein. For instance, pharmaceutically acceptable salts of compounds provided herein may be acid addition salts, base addition salts or metallic salts, and they can be synthesized from the parent compound which contains a basic or acidic moiety by conventional chemical methods. Generally, such salts are, for example, prepared by reacting the free acid or base forms of these compounds with a stoichiometric amount of the appropriate base or acid in water or in an organic solvent or in a mixture of the two. Generally, non-aqueous media like ether, ethyl acetate, ethanol, isopropanol or acetonitrile are preferred. Examples of the acid addition salts include mineral acid addition salts such as, for example, hydrochloride, hydrobromide, hydroiodide, sulphate, nitrate, phosphate, and organic acid addition salts such as, for example, acetate, maleate, fumarate, citrate, oxalate, succinate, tartrate, malate, mandelate, methanesulphonate and p-toluenesulphonate. Examples of the alkali addition salts include inorganic salts such as, for example, ammonium, and organic alkali salts such as, for example, ethylenediamine, ethanolamine, N,N-dialkylenethanolamine, triethanolamine, glucamine and basic aminoacids salts. Examples of the metallic salts include, for example, sodium, potassium, calcium, magnesium, aluminium and lithium salts.

In a more preferred embodiment, the BCL2 inhibitor is selected from the group consisting of venetoclax, navitoclax, Disarib, S55746, A1331852, WEHI-S39, Obatoclax, TW-37, AT101, Sabutoclax, A1210477, Umi-77, BTSA1, BAM7, MIM1, AMG-176, MIK665 (S64315), APG-1252, BXI-61 and BXI-72. In a preferred embodiment, the BCL2 inhibitor is selected form the group consisting of venetoclax and navitoclax. In a preferred embodiment, the BCL2 inhibitor is venetoclax, also known as GDC-0199, ABT-199, RG7601, CAS number 1257044-40-8, and its formula is depicted below (compound Ia). In another preferred embodiment, the BCL2 inhibitor is navitoclax, also known as ABT-263, CAS number 923564-51-6, and its formula is depicted below (compound Ib).

(Ia)

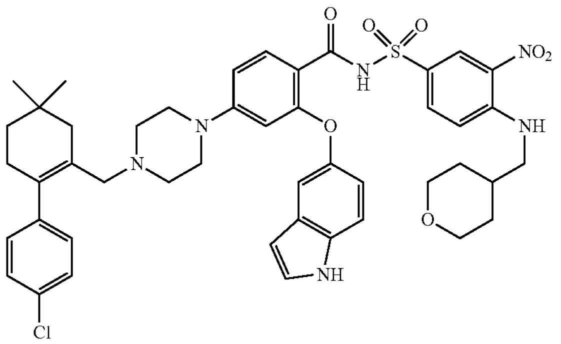

(Ib)

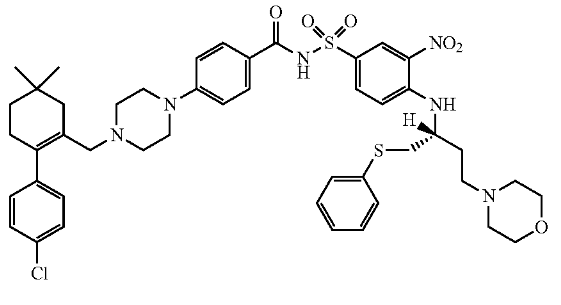

In a preferred embodiment the combination of the invention comprises an inhibitor of one or more members of the BCL-2 anti-apoptotic protein family selected from the group consisting of navitoclax or venetoclax and a carotenoid selected from the group consisting of fucoxanthin, fucoxanthinol, amarouciaxanthin A and neoxanthin.

Therefore, in a preferred embodiment, the combination of the invention comprises navitoclax and fucoxanthin, navitoclax and fucoxanthinol, navitoclax and amarouciaxanthin A, navitoclax and neoxanthin, venetoclax and fucoxanthin, venetoclax and fucoxanthinol, venetoclax and amarouciaxanthin A or venetoclax and neoxanthin.

In a more preferred embodiment the combination of the invention comprises an inhibitor of one or more members of the BCL-2 anti-apoptotic protein family selected from the group consisting of navitoclax or venetoclax and a carotenoid selected from the group consisting of fucoxanthin, fucoxanthinol and amarouciaxanthin A.

Therefore, in another more preferred embodiment, the combination of the invention comprises navitoclax and fucoxanthin, navitoclax and fucoxanthinol, navitoclax and amarouciaxanthin A, venetoclax and fucoxanthin, venetoclax and fucoxanthinol, or venetoclax and amarouciaxanthin A.

In another preferred embodiment, the combination of the invention comprises an activator of a BCL-2 pro-apoptotic family member.

"Activator of BCL-2 pro-apoptotic family members", as used herein relates to an activator of a class of pro-apoptotic proteins having BH1, BH2, and BH3 domains (BAX, BAK, and BOK); and pro-apoptotic BH3-only proteins (BIK, BAD, BID, BIM, BMF HRK, NOXA, and PUMA). In a preferred embodiment the activator of a BCL-2 pro-apoptotic family member is a synthetic peptide. In another preferred embodiment the activator is any compound that interacts with the surface pocket of BCL-2, such as HA14-1 or compound 106 as disclosed in Zhao G. et al., (Mol Cell Biol. 2014 April; 34 (7): 1198-1207).

Any method known in the art can be used to determine whether a compound is an activator of BCL-2 pro-apoptotic family member. The binding affinity of organic compounds to Bcl-2 protein in vitro may be determined by a competitive binding assay based for example on fluorescence polarization. In addition any method previously disclosed in relation to ability to inhibit the anti-apoptotic effect can be used to determine the ability of a compound of activating pro apoptosis.

In another preferred embodiment, the combination of the invention comprises an activator of BCL-2 pro-apoptotic family members and a carotenoid selected from the group consisting of fucoxanthin, fucoxanthinol, amarouciaxanthin A and neoxanthin.

The combinations of the invention show synergistic effects, for example in producing cytotoxic effects or reducing the number of senescent cells, so the same cytotoxic effect or senolytic or senomorphic effect is obtained with lower doses of an inhibitor of the BCL-2 anti-apoptotic protein family, an activator of BCL-2 pro-apoptotic family members, the senolytic agent or the senomorphic agent, respectively.

In a particular embodiment, the molar ratio of the carotenoid, the carotenoid metabolite, the carotenoid derivative, analogue or the ester or salt thereof and the second component selected from the group consisting of the inhibitor of one or more members of the BCL-2 anti-apoptotic protein family, the activator of BCL-2 pro-apoptotic family members, the senolytic agent and the senomorphic agent, in the combination is from 0.1:100 to 100:0.01, preferably from 0.2:100 to 100:0.05, more preferably from 0.5:100 to 100:0.1. In additional embodiments, the molar ratio of the carotenoid, the carotenoid metabolite, the carotenoid derivative, analogue or the ester or salt thereof and the second component selected from the group consisting of the inhibitor of one or more members of the BCL-2 anti-apoptotic protein family, the activator of BCL-2 pro-apoptotic family members, the senolytic agent and the senomorphic agent, in the combination is from 1:100 to 10:0,01, from 1:10 to 1:0,01, from 1:1 to 0,1:0,01 or from 0,1:1 to 1:1.

In the combination of the present invention the second component is not troglitazone and/or punicic acid.

Food, Cosmeceutical, Nutraceutical, Cosmetic or Pharmaceutical Composition

In another aspect, the invention relates to a food, a cosmeceutical, a nutraceutical, a cosmetic or pharmaceutical composition comprising a combination of the invention.

As used herein, the term "food" is any substance or product of any nature, solid or liquid, natural or processed which due to its characteristics, applications, components, preparation and state of preservation, can usually or ideally be used for some of the following purposes: a) as normal nutrition for human beings or animals or as pleasurable foods; or b) as dietetic products, in special cases of human or animal food (feed). The term "feed" includes all the natural materials and finished products of any origin which, separately or conveniently mixed with one another, are suitable as animal food.

A ready-to-eat food is that which does not need to be diluted by means of an aqueous solution suitable for consumption for example. In principle, the ingredients present in a ready-to-eat food are balanced and there is no need to add additional ingredients to the food to make it ready to eat, such considered by a person skilled in the art. A concentrated food is that in which one or more ingredients are present at a higher concentration than in a ready-to-eat food, therefore for use it is necessary to dilute it by means of an aqueous solution suitable for consumption for example. Non-limiting, illustrative examples of foods provided by this invention include both dairy products and derivatives, for example, fermented milks, yoghurt, kephir, curd, cheeses, butters, ice creams, milk-based desserts, etc., and non-dairy products, such as baked products, cakes and pastries, cereals, chocolates, jams, juices, other fruit derivatives, oils and margarines, prepared dishes, etc.

As used herein, the term "cosmeceutical product" refers to a product suitable for use in the body or animal body comprising one or more cosmeceutical products (functional cosmetics, dermaceuticals or active cosmetics), i.e., topical hybrid products with cosmetic-pharmaceutical characteristics containing active ingredients having effect on user's skin, hair and/or nails, at higher and more effective concentrations, therefore they are located in an intermediate level between cosmetic and drug. Illustrative examples of cosmeceutical products include essential oils, ceramides, enzymes, minerals, peptides, vitamins, etc.

As used herein, the term "nutraceutical product" refers to a product suitable for use in human beings or animals, comprising one or more natural products with therapeutic action which provide a health benefit or have been associated with disease prevention or reduction, and it includes dietary supplements presented in a non-food matrix (e.g., capsules, powder, etc.) of a concentrated natural bioactive product usually present (or not) in the foods and which, when taken in a dose higher than that existing in those foods, exerts a favorable effect on health which is greater than effect which the normal food may have. Therefore, the term "nutraceutical product" includes isolated or purified food products as well as additives or food supplements which are generally presented in dosage forms normally used orally, for example, capsules, tablets, sachets, drinkable phials, etc.; such products provide a physiological benefit or protection against diseases, generally against chronic diseases. If desired, the nutraceutical product provided by the invention can contain, in addition to the xanthophylls, one or more nutraceuticals (products or substances associated with disease prevention or reduction), for example, flavonoids, omega-3 fatty acids, etc., and/or one or more prebiotics (non-digestible food ingredients which stimulate probiotic activity and/or growth), for example, oligofructose, pectin, inulin, galacto-oligosaccharides, lactulose, human milk oligosaccharides, dietary fiber, etc.

As used herein, the term "nutritional composition" of the present invention relates to a food product that beneficially affects one or more functions of the body, so as to provide better health and wellness. Accordingly, such a nutritional composition may be intended for the prevention and/or treatment of a disease or a disease causing factor. Therefore, the term "nutritional composition" of the present invention can be used as a synonym for functional food or foods for particular nutritional purposes, or medical food. A nutritional composition is similar to that of a conventional food and consumed as part of a normal diet appearance.

The term "cosmetic composition" or "personal care composition", as used herein, refers to a composition suitable for use in personal hygiene of human beings or animals, or in order to enhance the natural beauty or change the body appearance without affecting the structure or functions of the human or animal body, comprising one or more products providing such effects. If desired, the cosmetic composition provided by the invention can contain, in addition to the combination of the invention, one or more cosmetics or cosmetic products, i.e., substances or mixtures intended to be placed in contact with the external parts of the human or animal body (e.g., epidermis, hair system, nails, lips, etc.) or with the teeth and the buccal mucosa, for the exclusive or main purpose of cleaning them, perfuming them, changing their appearance, protecting them, keeping them in good condition or correcting body odors. Illustrative examples of cosmetically acceptable vehicles include the products contained in the INCI (International Nomenclature of Cosmetic Ingredients) list. Cosmetic or personal care compositions include products such as balms, pads, pomades, creams, etc. oils, surfactants, humectants, botanical extracts, vitamins, antioxidants, sunscreen agents, perfumes, preservatives, and the like. Illustrative examples of humectants, botanical extracts, vitamins, antioxidants and sunscreen agents.

The ingredients as described hereinabove are preferably provided in a cosmetic composition that may be formulated into a cream, gel, lotion, oil, ointment, powder, stick, cake, or other forms that can be topically applied. The resulting cosmetic composition may be in the form of a liquid, solid, semi-solid, dispersion, suspension, solution or emulsion, and it can be either aqueous-based or anhydrous. The cosmetic compositions of the invention may also be in the form of color cosmetic compositions, such as foundation makeup, mascara, lip color, blush, eye shadow, and the like. Certain other derivatives are lipophilic in nature and will more likely be found in the oil phase of the emulsion. The combination of the invention is preferably found in the water phase of the emulsion or encapsulated in an aqueous phase within liposomes.

The term "cosmetic effective amount", as used herein, relates to the sufficient amount of a compound (i.e. of the combination of the invention) to provide the desired effect and it will generally be determined, by among other causes, the characteristics of the compound itself and the cosmetic effect to be achieved. The dosage for obtaining a cosmetic effective amount it will also depend on a range of factors, such as, for example, age, weight, sex or tolerance of the animal, preferably a mammal and more preferably human.

In a particular and preferred embodiment of the invention, the cosmetic composition of the invention is administered by topical route. Adequate formulations for topical administration of the composition of the invention are detailed in the context of the pharmaceutical compositions of the invention and equally apply to the cosmetic composition of the invention.

If desired, the cosmetic composition of the invention is incorporated in a fabric, a non-woven fabric or a medical device. Illustrative examples of said fabric, non-woven fabric or medical device include but are not limited to bandages, gauzes, t-shirts, panty hose, socks, underwear, girdles, gloves, diapers, sanitary napkins, dressings, bedspreads, towelettes, adhesive patches, non-adhesive patches, occlusive patches, microelectric patches and face masks.

Additionally, the invention also relates to a pharmaceutical composition comprising the combination of the invention.

The term "pharmaceutical composition", as used herein, relates to a composition comprising at least a combination provided by the present invention together with a pharmaceutically acceptable carrier.

The terms "pharmaceutically acceptable vehicle", "pharmaceutically acceptable carrier," "pharmaceutically acceptable diluent" or "pharmaceutically acceptable excipient", used interchangeably herein, refer to a non-toxic solid, semisolid or liquid filler, diluent, encapsulating material or formulation auxiliary of any conventional type. A pharmaceutically acceptable carrier is essentially non-toxic to recipients at the employed dosages and concentrations and is compatible with other ingredients of the formulation. The number and the nature of the pharmaceutically acceptable carriers depend on the desired administration form. The pharmaceutically acceptable carriers are known and may be prepared by methods well known in the art. They are involved in carrying or transporting the subject chemical from one organ, or portion of the body, to another organ, or portion of the body without excessive toxicity, irritation, allergic response, or other problem or complication, commensurate with a reasonable benefit/risk ratio. Each carrier must be "acceptable" in the sense of being compatible with the other ingredients of the formulation and not injurious to the patient. Some examples of materials which can serve as pharmaceutically-acceptable carriers include: (a) sugars (e.g. lactose, glucose and sucrose), (b) starches (e.g. corn starch and potato starch), (c) cellulose and its derivatives (e.g. sodium carboxymethyl cellulose, ethyl cellulose and cellulose acetate), (d) powdered tragacanth, (e) malt, (f) gelatin, (g) talc, (h) excipients (e.g. cocoa butter and suppository waxes), (i) oils (e.g. peanut oil, cottonseed oil, safflower oil, sesame oil, olive oil, corn oil and soybean oil), (j) glycols (e.g. propylene glycol), (k) polyols (e.g. glycerin, sorbitol, mannitol and polyethylene glycol), (l) esters (e.g. ethyl oleate and ethyl laurate), (m) agar, (n) buffering agents (e.g. magnesium hydroxide and aluminum hydroxide), (o) alginic acid, (p) pyrogen-free water, (q) isotonic saline, (r) Ringer's solution, (s) ethyl alcohol, (t) phosphate buffer solutions and (u) other non-toxic compatible substances employed in pharmaceutical formulations. Wetting agents, emulsifiers and lubricants (e.g. sodium lauryl sulfate and magnesium stearate), as well as coloring agents, release agents, coating agents, sweetening, flavoring and perfuming agents, preservatives and antioxidants can also be present in the compositions. Examples of pharmaceutically-acceptable antioxidants include: (a) water soluble antioxidants (e.g.

ascorbic acid, cysteine hydrochloride, sodium bisulfate, sodium metabisulfite or sodium sulfite), (b) oil-soluble antioxidants (e.g. ascorbyl palmitate, butylated hydroxyanisole (BHA), butylated hydroxytoluene (BHT), lecithin, propyl gallate or α-tocopherol), and (c) metal chelating agents (e.g. citric acid, ethylenediamine tetraacetic acid (EDTA), sorbitol, tartaric acid or phosphoric acid).

More preferably, the pharmaceutical product comprises a vehicle or carrier suitable for topical or oral administration.

Based on the particular mode of administration, the pharmaceutical product may be formulated into tablets, pills, capsules, sachets, granules, powders, suspensions, emulsions, anhydrous or hydrous topical formulations and solutions.

The pharmaceutical acceptable carriers or vehicles are well-known to those skilled in the art and are readily available to the public. It is preferred that the pharmaceutically acceptable carrier or vehicle be one which is chemically inert to the active formulation and each of its components and one which has no detrimental side effects or toxicity under the conditions of use.

In some embodiments, the pharmaceutical product is adapted as a delivery system for transporting the therapeutic agent orally, parenterally or intravenously into the circulatory system of a subject.

In cases other than intravenous administration, the composition can contain minor amounts of wetting or emulsifying agents, or pH buffering agents. The composition can be a liquid solution, suspension, emulsion, gel, polymer, or sustained release formulation. The composition can be formulated with traditional binders and carriers, as would be known in the art. Formulations can include standard carriers such as pharmaceutical grades of mannitol, lactose, starch, magnesium stearate, sodium saccharide, cellulose, magnesium carbonate, etc., inert carriers having well established functionality in the manufacture of pharmaceuticals. Various delivery systems are known and can be used to administer a therapeutic of the present invention including encapsulation in liposomes, microparticles, microcapsules and the like.

Where necessary, the combination or pharmaceutical composition of the invention, is comprised in a composition also including a solubilizing agent and a local anesthetic to ameliorate any pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the composition is to be administered by infusion, it can be dispensed with an infusion bottle containing sterile pharmaceutical grade water or saline. Where the combination is administered by injection, an ampule of sterile water for injection or saline can be provided so that the ingredients may be mixed prior to administration.

Formulations suitable for oral administration include liquid solutions, dissolved in diluents, such as water or saline; capsules, sachets, tablets, lozenges, each containing a predetermined amount of the combination of the invention; powders; suspensions in an appropriate liquid; and emulsions. Liquid dosage forms for oral administration may include emulsions, solutions, suspensions, syrups and elixirs pharmaceutically acceptable containing inert diluents commonly used in the technique, such as water. Those compositions may also comprise adjuvants such as wetting agents, emulsifying and suspending agents, and sweetening agents, flavoring and perfuming agents.

Solid dosage forms for oral administration may include conventional capsules, sustained release capsules, conventional tablets, sustained-release tablets, chewable tablets, sublingual tablets, effervescent tablets, pills, suspensions, powders, granules and gels. At these solid dosage forms, the active compounds can be mixed with at least one inert excipient such as sucrose, lactose or starch. Such dosage forms can also comprise, as in normal practice, additional substances other than inert diluents, e.g. lubricating agents such as magnesium stearate. In the case of capsules, tablets, effervescent tablets and pills, the dosage forms may also comprise buffering agents. Tablets and pills can be prepared with enteric coatings.

The parenteral formulations can be presented in unit-dose or multi-dose sealed containers, such as ampules and vials, and can be stored in freeze-dried (lyophilized) conditions requiring only the addition of the sterile liquid carrier, for example, water for injections, immediately prior to use.

The pharmaceutical composition of the invention can be administered by topical, transdermal or subcutaneous route. Illustrative examples of topical or transdermal administration include but are not limited to iontophoresis, sonophoresis, electroporation, mechanical pressure, osmotic pressure gradient, occlusive dressing, microinjections, needleless injections by means of pressure, microelectric patches and any combination thereof. In any case, the excipients will be chosen depending on the pharmaceutical dosage form selected.

Injectable preparations, for example, aqueous or oleaginous suspensions, sterile injectable may be formulated according with the technique known using suitable dispersing agents, wetting agents and/or suspending agents. Among the acceptable vehicles and solvents that can be used are water, Ringer's solution and isotonic sodium chloride solution. Sterile oils are also conventionally used as solvents or suspending media.

In a particular and preferred embodiment of the invention, the pharmaceutical composition of the invention is administered by topical route. For topical administration, the pharmaceutical compositions of the invention can be formulated as creams, gels, lotions, liquids, pomades, spray solutions, dispersions, solid bars, emulsions, microemulsions and similars which may be formulated according to conventional methods that use suitable excipients, such as, for example, emulsifiers, surfactants, thickening agents, coloring agents and combinations of two or more thereof.

Additionally, pharmaceutical compositions of the invention may be administered in the form of transdermal patches or iontophoresis devices. Suitable transdermal patches are well known by the person skilled in the art.

Several drug delivery systems are known and can be used to administer the combination of the invention, including, for example, encapsulation in liposomes, microbubbles, emulsions, microparticles, microcapsules, nanoparticles, nanocapsules and similars. The required dosage can be administered as a single unit or in a sustained release form. In a particular and preferred embodiment of the invention, the pharmaceutical composition is encapsulated in liposomes.

Sustainable-release forms and appropriate materials and methods for their preparation are well known in the state of the art. In one embodiment of the invention, the orally administrable form of a combination according to the invention is in a sustained release form further comprises at least one coating or matrix. The coating or sustained release matrix include, without limitation, natural polymers, semi-synthetic or synthetic water-insoluble, modified, waxes, fats, fatty alcohols, fatty acids, natural semisynthetic or synthetic plasticizers, or a combination of two or more of the them. Enteric coatings may be applied using conventional processes known to experts in the art.

All the terms and embodiments previously described in relation to the combination of the invention are equally applicable to this aspect of the invention.

Cosmetic Methods

The authors of the present invention have found that the combination of a carotenoid and senolytic agents, such as Bcl-2 inhibitors results in a synergistic senolytic effect. Thus, the invention also provides methods for the treatment of diseases in which there is an undesired accumulation of senescent cells, as well as for cosmetic methods wherein elimination of senescent cells is desired.

Thus, in another aspect, the invention relates to a cosmetic method for preventing and/or decreasing cutaneous senescence and/or for ameliorating the cosmetic adverse effects of aging comprising administering the combination according to the invention or the food, cosmeceutical, nutraceutical or cosmetic composition according to the invention to a subject in need thereof.

As used herein, the term "cosmetic method" relates to a method used to enhance the appearance of the skin in a subject. Cosmetic compositions used in the cosmetic method of the invention include skin-care creams, lotions, powders, lipsticks, eye and facial makeup, towelettes, gels, deodorants, hand sanitizer, baby products, bath oils, bubble baths, bath salts, butters and many other types of products.

Skin aging is a multi-factorial process that affects nearly every aspect of its biology and function; it is driven by both intrinsic (e.g., time, genetic factors, hormones) and extrinsic (e.g., UV exposure, pollution, cigarette smoke) factors. Skin aging is also produced by senescence.

Cellular senescence is a growth arrest that occurs as a result of different damaging stimuli, including DNA damage, telomere shortening and dysfunction or oncogenic stress. Senescent cells exert a pleotropic effect on development, tissue aging and regeneration, inflammation, wound healing and tumor suppression. Senescent cells are characterized by their inability to proliferate, resistance to apoptosis, and secretion of factors that promote inflammation and tissue deterioration.

Senescent keratinocytes and fibroblasts appear to accumulate with age in human skin. Moreover, senescent cells express genes that have long-range, pleiotropic effects-degradative enzymes, growth factors, and inflammatory cytokines.

"Cosmetic adverse effects of aging", as used herein relates to characteristics of intrinsic or chronological aging and include as a way of illustrative non limitative visible signs such as thin and dry skin, fine wrinkles, decreased elasticity, aberrant pigmentation, hair graying and hair loss.

"Cutaneous senescence", as used herein relates to means the state of growing old and particularly damage to the epidermal cells of human skin which results from partial damage or complete destruction of the cells, conversion of imide bonds to amide bonds in collagen and/or elastin caused by toxic byproducts of oxygen metabolism, free-radical pathology mechanisms or by photo-damage and generalized aging.

The cosmetic method of the invention is intended to decrease epidermal cell and thereby cutaneous senescence in a human by reducing or inhibiting senescence, including one or more affects such as reversing photo-damage or other regenerative effects, such as increasing underlying skin vascularity, increasing the rate of cellular replication and desquamation producing a more youthful appearance, increasing collagen synthesis and homogeneity, delaying cutaneous atrophy and thinning of epidermis and dermis, and the like.

The combination of the invention may be administered in a cosmetic effective amount. The term "cosmetic effective amount", as used herein, relates to the sufficient amount of a compound (i.e of the combination of the invention) to provide the desired effect and it will generally be determined, by among other causes, the characteristics of the compound itself and the cosmetic effect to be achieved. The dosage for obtaining a cosmetic effective amount it will also depend on a range of factors, such as, for example, age, weight, sex or tolerance of the animal, preferably a mammal and more preferably human.

In a particular and preferred embodiment of the cosmetic method of the invention, the cosmetic composition of the invention is administered by topical route. Adequate formulations for topical administration of the combination of the invention have been detailed in the context of the cosmetic compositions of the invention and equally apply to the cosmetic method of the invention.

If desired, the cosmetic composition of the invention is incorporated in a fabric, a non-woven fabric or a medical device. Illustrative examples of said fabric, non-woven fabric or medical device include but are not limited to bandages, gauzes, t-shirts, panty hose, socks, underwear, girdles, gloves, diapers, sanitary napkins, dressings, bedspreads, towelettes, adhesive patches, non-adhesive patches, occlusive patches, microelectric patches and face masks.

All the terms and embodiments previously described are equally applicable to this aspect of the invention.

Medical Uses

In another aspect, the invention relates to the combination according to the invention or the pharmaceutical composition according to the invention for use in medicine.

The compositions according to the invention, when used in medicine, can be used by either, simultaneous administration or by any manner of separate or sequential administration of a therapeutically effective amount of of (i) a carotenoid, a carotenoid metabolite, a carotenoid derivative, analogue or an ester or salt thereof and (ii) an inhibitor of one or more members of the BCL-2 anti-apoptotic protein family, an activator of BCL-2 pro-apoptotic family members, a senolytic agent or a senomorphic agent. The term "combination" also stands for the various combinations of compounds (i) and (ii), for example in a single composition, in a combined mixture composed from separate formulations of the single active compounds, such as a "tank-mix", and in a combined use of the single active ingredients when applied in a sequential manner, i.e. one after the other with a reasonably short period, such as a few hours or days or in simultaneous administration.

Preferably, if the administration is not simultaneous, the compounds are administered in a close time proximity to each other. Furthermore, it does not matter if the compounds are administered in the same dosage form or by the same route, e.g. one compound may be administered topically and the other compound may be administered orally. Suitably, both compounds are administered orally.

The combination of the invention may be formulated for its simultaneous, separate or sequential administration. This has the implication that the combination of the two compounds may be administered:

as a combination that is being part of the same medicament formulation, the two compounds being then administered always simultaneously.

as a combination of two units, each with one of the substances giving rise to the possibility of simultaneous, sequential or separate administration.

In a particular embodiment, the carotenoid, carotenoid metabolite, carotenoid derivative, analogue or an ester or salt thereof is independently administered from the senolytic agent, the senomorphic agent, the inhibitor of one or more members of the BCL-2 anti-apoptotic protein family or the activator of BCL-2 pro-apoptotic family members (i.e in two units) but at the same time.

In another particular embodiment, the carotenoid, carotenoid metabolite, carotenoid derivative, analogue or an ester or salt thereof is administered first, and then the senolytic agent, the senomorphic agent, the inhibitor of one or more members of the BCL-2 anti-apoptotic protein family or the activator of BCL-2 pro-apoptotic family members is separately or sequentially administered.

In yet another particular embodiment, the senolytic agent, the senomorphic agent, the inhibitor of one or more members of the BCL-2 anti-apoptotic protein family or the activator of BCL-2 pro-apoptotic family members is administered first, and then the carotenoid, a carotenoid metabolite, a carotenoid derivative, analogue or an ester or salt thereof is administered, separately or sequentially, as defined.

In another aspect, the invention relates to a combination according to the invention or the pharmaceutical composition according to the invention for use in the treatment of cancer.

Alternatively, the invention relates to a method for preventing and/or treating a cancer comprising administering the combination according to the invention or the pharmaceutical composition according to the invention to a subject in need thereof.

Alternatively, the invention relates to the use of a combination according to the invention or the pharmaceutical composition according to the invention for the preparation of a medicament for preventing and/or treating cancer in a subject in need thereof.

The term "prevention", "preventing" or "prevent", as used herein, relates to the administration of a combination according to the invention or of a medicament comprising said combination to a subject who has not been diagnosed as possibly having a cancer as an example, but who would normally be expected to develop said disease or be at increased risk for said disease. The prevention intends to avoid the appearance of said disease. The prevention may be complete (e.g. the total absence of a disease). The prevention may also be partial, such that for example the occurrence of a disease in a subject is less than that which would have occurred without the administration of the composition of the present invention. Prevention also refers to reduced susceptibility to a clinical condition.

The term "treatment", as used herein, refers to any type of therapy, which is aimed at terminating, preventing, ameliorating or reducing the susceptibility to a clinical condition as described herein. In a preferred embodiment, the term treatment relates to prophylactic treatment (i.e. a therapy to reduce the susceptibility to a clinical condition), of a disorder or a condition as defined herein. Thus, "treatment," "treating," and their equivalent terms refer to obtaining a desired pharmacologic or physiologic effect, covering any treatment of a pathological condition or disorder in a mammal, including a human. The effect may be prophylactic in terms of completely or partially preventing a disorder or symptom thereof and/or may be therapeutic in terms of a partial or complete cure for a disorder and/or adverse effect attributable to the disorder. That is, "treatment" includes (1) preventing the disorder from occurring or recurring in a subject, (2) inhibiting the disorder, such as arresting its development, (3) stopping or terminating the disorder or, at least, symptoms associated therewith, so that the host no longer suffers from the disorder or its symptoms, such as causing regression of the disorder or its symptoms, for example, by restoring or repairing a lost, missing or defective function, or stimulating an inefficient process, or (4) relieving, alleviating, or ameliorating the disorder, or symptoms associated therewith, where ameliorating is used in a broad sense to refer to at least a reduction in the magnitude of a parameter.

The term "cancer" as used herein, refers to a disease characterized by uncontrolled cell division (or by an increase of survival or apoptosis resistance) and by the ability of said cells to invade other neighbouring tissues (invasion) and spread to other areas of the body where the cells are not normally located (metastasis) through the lymphatic and blood vessels, circulate through the bloodstream, and then invade normal tissues elsewhere in the body. Depending on whether or not they can spread by invasion and metastasis, tumours are classified as being either benign or malignant: benign tumours are tumours that cannot spread by invasion or metastasis, i.e., they only grow locally; whereas malignant tumours are tumours that are capable of spreading by invasion and metastasis. As used herein, the term cancer includes, but is not limited to, the following types of cancer: breast cancer; biliary tract cancer; bladder cancer; brain cancer including glioblastomas, in particular glioblastoma multiforme, and medulloblastomas; cervical cancer; head and neck carcinoma; choriocarcinoma; colon cancer, colorectal cancer; endometrial cancer; esophageal cancer; gastric cancer; hematological neoplasms including acute lymphocytic and myelogenous leukemia; T-cell acute lymphoblastic leukemia/lymphoma; hairy cell leukemia; chronic myelogenous leukemia, multiple myeloma; AIDS-associated leukemias and adult T-cell leukemia/lymphoma; intraepithelial neoplasms including Bowen's disease and Paget's disease; liver cancer, hepatoma; lung cancer, pleural mesothelioma; lymphomas including Hodgkin's disease and lymphocytic lymphomas; neuroblastomas; oral cancer including squamous cell carcinoma; parotid gland cancer; ovarian cancer including those arising from epithelial cells, stromal cells, germ cells and mesenchymal cells; pancreatic cancer; prostate cancer; kidney cancer, suprarenal cancer; rectal cancer; sarcomas including leiomyosarcoma, rhabdomyosarcoma, liposarcoma, fibrosarcoma, and osteosarcoma; skin cancer including melanoma, Merkel cell carcinoma, Kaposi's sarcoma, basal cell carcinoma, and squamous cell cancer; cervix cancer, endometrial cancer; testicular cancer including germinal tumors such as seminoma, non-seminoma (teratomas, choriocarcinomas), stromal tumors, and germ cell tumors; thyroid cancer including thyroid adenocarcinoma and medullar carcinoma; and renal cancer including adenocarcinoma and Wilms tumor. Other cancers will-be known to one of ordinary skill. In a preferred embodiment, the cancer is a hematological cancer or a hematological malignancy. The term "hematological cancer or haematological malignancy" refers to types of cancer that affect blood, bone marrow, and lymph nodes. Haematological malignancies may derive from either of the two major blood cell lineages: myeloid and lymphoid cell lines. The myeloid cell line normally produces granulocytes, erythrocytes, thrombocytes, macrophages and mast cells; the lymphoid cell line produces B, T, NK and plasma cells. Lymphomas, lymphocytic leukaemias, and myelomas are from the lymphoid line, while acute and chronic myelogenous leukaemia, myelodysplastic syndromes (MDS) and myeloproliferative diseases are myeloid in origin. Non limitative, illustrative examples of haematological malignancies are Acute lymphoblastic leukaemia (ALL), Acute myelogenous leukaemia (AML), Chronic lymphocytic leukaemia (CLL), Chronic myelogenous leukaemia (CML), Acute monocytic leukaemia (AMOL), Hodgkin's lymphomas, non-Hodgkin's lymphomas (NHL) and myelomas such as multiple myeloma (MM). In a more preferred embodiment, the hematological malignancy is leukemia. In a more preferred embodiment the leukemia is from myeloid origin. In a more preferred embodiment, the leukemia is acute myeloid leukaemia. In another preferred embodiment, the hematologic cancer is AML, NHL, MDS, MM, CLL or myelofibrosis.

In another preferred embodiment, the cancer is breast cancer, lung cancer, melanoma, pancreatic cancer, colon cancer, kidney cancer, basal cell carcinoma, squamous cell carcinoma, relapsed or refractory malignancies, prostate cancer, neuroblastoma, glioblastoma, astrocytoma or ovarian cancer. In a preferred embodiment, the cancer is skin cancer, more preferably melanoma.

The authors of the present invention have shown that the combined use of a carotenoid and a senolytic agent leads to a synergistic senolytic effect. Thus, the invention also provides the use of these compositions for the treatment of diseases which require the selective destruction of senescent cells.

In another aspect, the invention relates to a combination according to the invention or the pharmaceutical composition according to the invention for use in the prevention and/or treatment of a senescence-associated disease or disorder.

Alternatively, the invention relates to a method for preventing and/or treating a senescence-associated disease or disorder comprising administering a combination or a pharmaceutical composition according to the invention.

Alternatively, the invention relates to a combination or pharmaceutical composition of the invention for the preparation of a medicament for preventing and/or treating a senescence-associated disease or disorder.

"Senescence-associated disease or disorder" as used herein relates to a clinical condition in which the presence and action of senescent cells contributes substantially to the pathophysiology of the condition.

In another preferred embodiment, the senescence-associated disease or disorder is fibrosis.

"Fibrosis" as used herein relates to is the formation of excess fibrous connective tissue in an organ or tissue in a reparative or reactive process. Although fibrosis may be a benign state, the present invention relates preferably to fibrosis in a pathological state. In a preferred embodiment the fibrosis is characterized by having a high number of senescent cells.

In another preferred embodiment, the fibrosis having high number of senescent cells is lung fibrosis, chronic obstructive pulmonary disease, myocardial fibrosis, renal fibrosis, myelofibrosis or liver fibrosis.

"High number of senescent cells", as used herein refers that the number of senescent cells in the tissue suffering fibrosis is increased with respect to the number of cells in a normal tissue. In a preferred embodiment, the number of senescent cells in the tissue suffering fibrosis is at least 1.1-fold, 1.5-fold, 5-fold, 10-fold, 20-fold, 30-fold, 40-fold, 50-fold, 60-fold, 70-fold, 80-fold, 90-fold, 100-fold or even more compared with the number of senescent cells in a normal tissue. By normal tissue is meant a tissue not suffering fibrosis.

A senescent cell may exhibit any one or more of the following characteristics. (I) Senescence growth arrest is essentially permanent and cannot be reversed by known physiological stimuli. (2) Senescent cells increase in size, sometimes enlarging more than two fold relative to the size of non-senescent counterparts. (3) Senescent cells express a senescence-associated P-galactosidase (SAP-gal), which partly reflects the increase in lysosomal mass. (4) Most senescent cells express p16INK4a, which is not commonly expressed by quiescent or terminally differentiated cells. (5) Cells that senesce with persistent DDR signaling harbor persistent nuclear foci, termed DNA segments with chromatin alterations reinforcing senescence (DNA-SCARS). These foci contain activated DDR proteins and are distinguishable from transient damage foci. DNA-SCARS include dysfunctional telomeres or telomere dysfunction-induced foci (TIF). (6) Senescent cells express and may secrete molecules called herein senescent cell-associated molecules, which in certain instances may be observed in the presence of persistent DDR signaling.

The presence of senescent cells in a tissue may be detected though the presence of senescent cell-associated molecules that include growth factors, proteases, cytokines (e.g., inflammatory cytokines), chemokines, cell-related metabolites, reactive oxygen species (e.g., H2O2), and other molecules that stimulate inflammation and/or other biological effects or reactions that may promote or exacerbate the underlying disease of the subject. In a preferred embodiment, senescent cells are detected by detecting senescence-associated secretory phenotype (SASP, i.e., which includes secreted factors which may make up the pro-inflammatory phenotype of a senescent cell), senescent-messaging secretome, and DNA damage secretory program (DDSP).

Senescent cells and senescent cell associated molecules can be detected by techniques and procedures described in the art. For example, the presence of senescent cells in tissues can be analyzed by histochemistry or immunohistochemistry techniques that detect the senescence marker, SA-beta galactosidase (SA-Pgal) (see, e.g., Dimri et al, *Proc. Natl. Acad. Sci. USA* 92:9363-9367 (1995)). The presence of the senescent cell-associated polypeptide pI6 can be determined by any one of numerous immunochemistry methods practiced in the art, such as immunoblotting analysis. Expression of pI6 mRNA in a cell can be measured by a variety of techniques practiced in the art including quantitative PCR. The presence and level of senescent cell associated polypeptides (e.g., polypeptides of the SASP) can be determined by using automated and high throughput assays, such as an automated Luminex array assay described in the art (see, e.g., Coppe et al, *PLoS Biol* 6:2853-68 (2008)). The presence of senescent cells can also be determined by detection of senescent cell-associated molecules, which include growth factors, proteases, cytokines (e.g., inflammatory cytokines, such as determining the level of IL-1β as in Example 4), chemokines, cell-related metabolites, reactive oxygen species (e.g., $H_2O_2$) and other molecules that stimulate inflammation and/or other biological effects or reactions that may promote or exacerbate the underlying disease of the subject.

Senescence-associated diseases and disorders include, for example, cardiovascular diseases and disorders, inflammatory diseases and disorders, autoimmune diseases and disorders, pulmonary diseases and disorders, eye diseases and disorders, metabolic diseases and disorders, neurological diseases and disorders (e.g., neurodegenerative diseases and disorders); age-related diseases and disorders induced by senescence; skin conditions; age-related diseases; dermatological diseases and disorders; and transplant related diseases and disorders.

In another specific embodiment, the senescence-associated disease or disorder is a cardiovascular disease selected from atherosclerosis, angina, arrhythmia, cardiomyopathy, congestive heart failure, coronary artery disease, carotid artery disease, endocarditis, coronary thrombosis, myocardial infarction, hypertension, aortic aneurysm, cardiac diastolic dysfunction, hypercholesterolemia, hyperlipidemia, mitral valve prolapsed, peripheral vascular disease, cardiac stress resistance, cardiac fibrosis, brain aneurysm, and stroke. In another specific embodiment, the senescence-associated disease or disorder is an inflammatory or autoimmune disease or disorder selected from osteoarthritis, osteoporosis, oral mucositis, inflammatory bowel disease, kyphosis, and herniated intervertebral disc. In another specific embodiment, the senescence-associated disease or disorder is a neurodegenerative disease selected from Alzheimer's disease, Parkinson's disease, Huntington's disease, dementia, mild cognitive impairment, and motor neuron dysfunction. In another specific embodiment, the senescence-associated disease or disorder is a metabolic disease selected from diabetes, diabetic ulcer, metabolic syndrome, and obesity. In another specific embodiment, the senescence associated disease or disorder is a pulmonary disease selected from pulmonary fibrosis, chronic obstructive pulmonary disease, asthma, cystic fibrosis, emphysema, bronchiectasis, and age-related loss of pulmonary function. In another specific embodiment, the senescence-associated disease or disorder is an eye disease or disorder selected from macular degeneration, glaucoma, cataracts, presbyopia, and vision loss. In another specific embodiment, the senescence-associated disease or disorder is an age-related disorder selected from renal disease, renal failure, frailty, hearing loss, muscle fatigue, skin conditions, skin wound healing, liver fibrosis, pancreatic fibrosis, oral submucosa fibrosis, and sarcopenia. In another specific embodiment, the senescence-associated disease or disorder is a dermatological disease or disorder is selected from eczema, psoriasis, hyperpigmentation, nevi, rashes, atopic dermatitis, urticaria, diseases and disorders related to photosensitivity or photoaging, rhytides; pruritis; dysesthesia; eczematous eruptions; eosinophilic dermatosis; reactive neutrophilic dermatosis; pemphigus; pemphigoid; immunobullous dermatosis; fibrohistocytic proliferations of skin; cutaneous lymphomas; and cutaneous lupus. In another specific embodiment, the senescence-associated disease or disorder is atherosclerosis; osteoarthritis; pulmonary fibrosis; hypertension, chronic obstructive pulmonary disease; myelofibrosis; or liver fibrosis.

In a preferred embodiment, the senescence-associated disease or disorder is selected from the group consisting of cancer, fibrosis and chemotherapy- or radiotherapy-induced senescence.

In a preferred embodiment, the senescence-associated disease or disorder is cancer, more preferably a hematologic cancer or skin cancer.

In another preferred embodiment, the fibrosis having high number of senescent cells is lung fibrosis, chronic obstructive pulmonary disease, myocardial fibrosis, renal fibrosis, myelofibrosis or liver fibrosis.

In another preferred embodiment, the senescence disorder is therapy-induced senescence, preferably chemotherapy- or radiotherapy-induced senescence. In a more preferred embodiment, the therapy-induced senescence in cancer. Illustrative non-limitative examples of cancer have been previously described.

"Therapy-induced senescence", or TIS, as used herein relates to the senescence induced by therapy. DNA damaging radiotherapy and chemotherapies can induce a SASP in vivo (see, e.g., Coppe et al, 2008, PLoS Biol. 6:2853-2868), which can have deleterious systemic effects, as well as the ability to stimulate the re-growth of tumor cells that were not eradicated by the anti-cancer therapy. Unlike apoptotic cell death, with its remainders rapidly being cleared by phagocytosis without much of an inflammatory response, senescent cells may persist for varying periods of time at the tumor site.

Several assays can be used to determine the presence of therapy induced senescence such as SA-β-gal assay, Ki67 and/or H3K9me3 staining or determination of an increase in IL-1 β.

In a preferred embodiment the therapy is radiation or chemotherapy. In a preferred embodiment, the radiotherapy is gamma irradiation.

"Chemotherapy" relates to the treatment using a chemotherapeutic agent. The term "chemotherapeutic agent" includes standard chemotherapy drugs, which generally attack any quickly dividing cell, targeted therapy agents and immunomodulatory agents. Illustrative non-limitative examples of cancer chemotherapeutic agents which may be in accordance to the present invention include alkylating agents, antimetabolite drugs, anthracycline antibiotics, antibodies targeted against proangiogenic factors, topoisomerase inhibitors, antimicrotubule agents, inhibitors of cyclin-dependent kinases, low molecular weight tyrosine kinases inhibitors of proangiogenic growth factors and matrix metalloproteinase inhibitors.

In a more preferred embodiment the chemotherapy agent is selected from the group consisting of Aphidocolin, Bleomycin, Camptothecin, Carboplatin, docetaxel, Cisplatin, Cyclophosphamide, daunorubicin, doxorubicin, cytarabine, palbociclib, 5-Fluorouracil, Diaziquone/AZQ, Epigallocatechin gallate, Etoposide, Hydroxyurea, K858, Lovastatin, Mitoxantrone, MLN4924, MLN8054, Pyrithione, Resveratrol, TPA, PEP005, PEP008 and VO-OHpic.

In a more preferred embodiment, the chemotherapeutic agent is doxorubicin. In another preferred embodiment, the chemotherapeutic agent is palbociclib.

For the medical uses of the invention, the combination of the invention or the pharmaceutical composition comprising said combination may be administered in a therapeutically effective amount.

The term "therapeutically effective amount", as used herein, relates to the sufficient amount of a compound (i.e. of the combination of the invention) to provide the desired effect and it will generally be determined, by among other causes, the characteristics of the compound itself and the therapeutic effect to be achieved. It will also depend on the subject to be treated, the severity of the disease suffered by said subject, the chosen dosage form, administration route, etc. For this reason, the person skilled in the art must adjust the doses depending on the aforementioned variables.

For the medical uses of the invention, the combination or the pharmaceutical composition of the invention may be administered by any administration route, for example, by systemic (e.g. intravenous, subcutaneous, intramuscular injection), oral, parenteral (intranasal, sublingual) or topical administration.

There have been numerous reports across several cancer types that senescence is associated with poor a therapeutic index to cancer therapeutics.

It is well known in the art that many tumor cells become resistant to chemotherapy by entering into senescence and that, once the chemotherapy is removed, the cells leave senescence and resume proliferation or induce the proliferation of neighboring cells (see e.g. Gordin and Nelson, Drug Resist Updat. 2012, 15:123-131). Thus, the compositions according to the invention, in view of their senolytic effect may be used in order to destroy cells that have entered senescence in response to a chemotherapy treatment, thereby resulting in increased efficacy of the chemotherapy treatment. Thus, in another aspect the invention relates to the combination according to the invention or the food, nutraceutical or pharmaceutical composition according to the invention for use in enhancing the effectiveness of an antitumoral compound.

"Enhancing the effectiveness", as used herein includes augmenting, intensifying, accentuating, magnifying and potentiating the effect produced by an antitumoral compound.

As the combination of the invention reduces the senescence induced by therapy, this results in an improvement or increase of the medical therapy's therapeutic and/or prophylactic benefit compared with the benefit observed in the absence of administering the agent. Therefore, a particular dose of the antitumoral compound together with the combination of the invention led to a higher effect compared to the same dose of antitumoral compound in the absence of the administration of the combination of the invention to the same subject.

All the terms and embodiments previously described in relation to the combination of the invention are equally applicable to these aspects of the invention.

Medical Uses of Carotenoids

The authors of the present invention have shown that carotenoids are capable of reverting the senescent phenotype induced by cytotoxic agents (see example 3). Thus, this allows the use of carotenoids for the treatment of those diseases which are characterized by an undesired number of senescent cells by promoting the cells to abandon the senescent phenotype. Thus, in another aspect, the invention relates to a carotenoid, carotenoid metabolite, carotenoid derivative, analogue or an ester or salt thereof for use in the treatment of a senescence-associated disease or disorder.

Alternatively, the invention relates to the use of a carotenoid, carotenoid metabolite, carotenoid derivative, analogue or an ester or salt thereof for the preparation of a medicament for the treatment of a senescence-associated disease or disorder.

Alternatively, the invention relates to a method for treating a senescence-associated disease or disorder comprising administering a carotenoid, carotenoid metabolite, carotenoid derivative, analogue or an ester or salt thereof to a subject in need thereof. The term "senescence-associated disease or disorder" and its embodiments have been previously described and are equally application to this aspect of the invention.

In a preferred embodiment the senescence-associated disease or disorder is cancer, more preferably a hematologic cancer or skin cancer.

In another preferred embodiment, the senescence-associated disease or disorder is fibrosis. In a preferred embodiment the fibrosis is characterized as having high number of senescent cells.

In another preferred embodiment, the fibrosis having high number of senescent cells is lung fibrosis, chronic obstructive pulmonary disease, myocardial fibrosis or renal fibrosis.

In another preferred embodiment the senescence disorder is therapy-induced senescence, more preferably chemotherapy- or radiotherapy-induced senescence.

In a preferred embodiment, the carotenoid is selected from the group consisting of fucoxanthin, fucoxanthinol, amarouciaxanthin A, neoxanthin, astaxanthin, zeaxanthin and lutein. In a preferred embodiment, the carotenoid is fucoxanthin. In another preferred embodiment, the carotenoid is amarouciaxanthin A. In another preferred embodiment, the carotenoid is not fucoxanthin. In another preferred embodiment, the carotenoid is not fucoxanthinol. In another preferred embodiment, the carotenoid is not amarouciaxanthin A. In another preferred embodiment, the carotenoid is not neoxanthin. In another preferred embodiment, the carotenoid is not astaxanthin. In another preferred embodiment, the carotenoid is not zeaxanthin. In another preferred embodiment, the carotenoid is not lutein.

In another aspect, the invention relates to a carotenoid, a carotenoid metabolite, carotenoid derivative, analogue or an ester or salt thereof for use in enhancing the effectiveness of an antitumoral compound.

In addition, it is well known that certain antitumoral agents cause secondary effects due to the induction of senescence in non-tumor cells (see Demaria, Mol. Cell Oncol. 2017; 4 (3): e1299666.). Thus, the capability of the carotenoids to promote the exit of the cells from the senescent phenotype allows the use of the carotenoids for reducing the adverse effect of antitumoral treatments. Accordingly, in another aspect, the invention relates to a carotenoid, a carotenoid metabolite, carotenoid derivative, analogue or an ester or salt thereof for use in reducing the adverse effect of an antitumoral treatment.

"Adverse effect", side effects, toxic side effects or deleterious side effects as used herein relates to an undesired harmful effect resulting from a medication with an antitumoral compound. Preferably the adverse effect is gastrointestinal toxicity, peripheral neuropathy, fatigue, malaise, low physical activity, hematological toxicity, hepatotoxicity, alopecia, pain, mucositis, fluid retention, dermatological toxicity, fatigue or cardiotoxicity.

"Reducing adverse effects" as used herein, relates to the likelihood that said adverse effect appear is lower compared to a subject not receiving the carotenoid, carotenoid metabolite, carotenoid derivative, analogue or an ester or salt thereof, or that the adverse effect is of lower intensity compared to the a subject not receiving the carotenoid, a carotenoid metabolite, carotenoid derivative, analogue or an ester or salt thereof.

In a preferred embodiment, the likelihood of adverse effect in the subject being treated with an antitumoral compound is reduced by at least 10%, at least 15%, at least 20%, at least 25%, at least 30%, at least 35%, at least 40%, at least 45%, at least 50% or at least 55%.

The likelihood of suffering adverse effect of reducing an adverse effect may be measure by methods known in the art depending on the adverse effect to be determined.

In a preferred embodiment, the adverse effect is due to a chemotherapy treatment. In another preferred embodiment the adverse effect is due to a radiotherapy treatment.

All the terms and embodiments previously described in relation to the combination of the invention are equally applicable to these aspects of the invention.

Method for Inhibiting Senescence

In another aspect, the invention relates to a method for inhibiting senescence in a cell population or a subject which comprises administering a carotenoid, carotenoid metabolite, carotenoid derivative, analogue or an ester or salt thereof in an effective amount to the cell population or subject in need thereof.

"Inhibiting" as used herein relates to reducing or decreasing senescence. "Decrease" as used herein, relates to a reduction of senescence more than at least 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 99%, or 100% compared to the level of senescence in the absence of administration of a carotenoid, carotenoid metabolite, carotenoid derivative, analogue or an ester or salt thereof.

Methods for determining senescence have been previously described. In a preferred embodiment, the level of senescence is determined by detecting the number of senescent cells. In another preferred embodiment, the level of senescence is determined by quantifying the number of a senescence marker.

The method for inhibiting senescence in a cell population of the invention comprises a first step of contacting the cell population with the carotenoid, carotenoid metabolite, carotenoid derivative, analogue or an ester or salt thereof. In the case wherein the cell population forms part of an individual, then the contacting step can be carried by administering a carotenoid, carotenoid metabolite, carotenoid derivative, analogue or an ester or salt thereof to the individual. Any method for administering the carotenoid, carotenoid metabolite, carotenoid derivative, analogue or an ester or salt thereof previously describe may be used. The level of senescent cells may be determined according to any of the in vitro assays or techniques known in the art. For example, senescent cells may be detected by morphology (as viewed by microscopy, for example); production of senescence associated markers such as, senescence-associated β-galactosidase (SA-β-gal), p16INK4a, p21, PAI-I, or any one or more SASP factors (e.g., IL-6, MMP3).

Additionally, the method for inhibiting senescence comprises a second step of measuring the level of senescence and comparing it with a reference value.

"Reference value", as used herein relates to a laboratory value used as a reference for the values/data obtained from samples. The reference value (or reference level) can be an absolute value, a relative value, a value which has an upper and/or lower limit, a series of values, an average value, a median, a mean value, or a value expressed by reference to a control or reference value. A reference value can be based on the value obtained from an individual sample, such as, for example, a value obtained from a sample of study but obtained at a previous point in time. The reference value can be based on a high number of samples, such as the values obtained in a population of samples or based on a pool of samples including or excluding the sample to be tested. In a particular embodiment, the reference value is the level of senescence in a cell or subject in the absence of the same carotenoid, carotenoid metabolite, carotenoid derivative, analogue or an ester or salt thereof.

All the terms and embodiments previously described in relation to the combination of the invention are equally applicable to these aspects of the invention.

The following examples illustrate the invention and must not be considered as limiting the same.

EXAMPLES

Example 1—Synergy of Carotenoids and BCL2 Inhibitors in Cancer

Materials and Methods

Cell Cultures

Human MV-4-11 and PL-21 cell lines were used to evaluate fucoxanthin and amarouciaxanthin A effects in combination with the BCL-2 family inhibitor Navitoclax (ABT-263) and Venetoclax (ABT-199). Cells were cultured in RPMI media supplemented with 10% FCS at 37° C. in a humidified 5% $CO_2$-atmosphere, and were consistently free of mycoplasma, as evaluated by PCR. All passages were performed between 80 and 90% of confluence and with viability above 90%.

MTT Assay

For cytotoxicity determination, MV-4-11 cells and PL-21 cells were plated in 96-well microplates at a density of $10^4$ cells/well. After 24 hours, different concentration combinations of Navitoclax or Venetoclax and fucoxanthin or amarouciaxanthin A were added. Plates were incubated for 72 hours at 37° C. and 5% $CO_2$. DMSO was used as vehicle control. After this period, 50 μL of SDS 10% were added to the negative control wells (0% viability, 100% mortality). Then, culture media was replaced by fresh media with 10 μL of MTT 5 mg/ml in PBS in each well. Plates were incubated for 4 hours at 37° C. and 5% $CO_2$. Next, culture media was removed and 100 μL of extraction buffer (SDS, DSA, acetic acid 2%, pH 4.7) were added to each well. After incubating plates for 1 hour at 37° C. and 5% $CO_2$, cultures were homogenized. Finally, plates were read at 570 nm with the spectrophotometer Multiskan Ascent (MTX Lab systems). The potency of each product was determined through the calculation of IC50 (half maximal inhibitory concentration).

Results

In order to test fucoxanthin and amarouciaxanthin A cytotoxic effects in combination with different drugs (BCL2 inhibitors) in cancer cells, an array of concentrations of fucoxanthin were co-incubated with the following compounds:

Navitoclax (ABT-263)

Venetoclax (ABT-199)

The cytotoxic potency of each compound, as well as their combined potency with fucoxanthin, was obtained in an MTT assay in MV-4-11 and PL-21 cells. This parameter is expressed in terms of IC50 in Table 1. The different synergic combination scores were also obtained and are shown in Table 2 for MV-4-11 cells and Table 3 for PL-21 cells.

TABLE 1

IC50 of different drugs in two hematologic cancer cell lines (6 replicates).

| Drug | Cell line | IC50 (μM) (mean ± SD) |
|---|---|---|
| Navitoclax | MV-4-11 | 0.14 ± 0.01 |
| | PL-21 | 1.22 ± 0.12 |
| Venetoclax | MV-4-11 | $4.8 \times 10^{-3} \pm 1.3 \times 10^{-3}$ |
| Amarouciaxanthin A | MV-4-11 | 1.45 ± 0.27 |
| Fucoxanthin | MV-4-11 | 1.34 ± 0.07 |
| | PL-21 | 10.53 ± 1.55 |

SD, standard deviation.

TABLE 2

Synergy scores of different drug combinations with fucoxanthin in MV-4-11 cells. Combination indexes were calculated following the Chou-Talalay method (Cancer Res. 2010 Jan 15;70(2):440-6.). Values are interpreted as follows: <1 synergism, >1 antagonism, and =1 additive effect.

| Compound 1 | Compound 2 | Conc 1 (μM) | Conc 2 (μM) | CI at IC50 | CI at IC25 |
|---|---|---|---|---|---|
| Fucoxanthin | Navitoclax | 0.5 | 0-100 | 0.89 | 0.58 |
| Fucoxanthin | Navitoclax | 0.3 | 0-100 | 0.84 | 0.57 |
| Amarouciaxanthin A | Navitoclax | 1 | 0-100 | 0.83 | 0.28 |
| Amarouciaxanthin A | Navitoclax | 0.5 | 0-100 | 0.58 | 0.28 |
| Amarouciaxanthin A | Navitoclax | 0.3 | 0-100 | 0.57 | 0.35 |
| Fucoxanthin | Venetoclax | 1 | 0-100 | 0.80 | 0.44 |

Conc, concentration; CI, Combination Index

TABLE 3

Synergy scores of different drug combinations with fucoxanthin in PL-21 cells. Combination indexes were calculated following the Chou-Talalay method cited supra. Values are interpreted as follows: <1 synergism, <1 antagonism, and =1 additive effect.

| Compound 1 | Compound 2 | Conc 1 (μM) | Conc 2 (μM) | CI at IC50 | CI at IC25 |
|---|---|---|---|---|---|
| Fucoxanthin | Navitoclax | 6 | 0-100 | 0.72 | 0.31 |
| Fucoxanthin | Navitoclax | 3 | 0-100 | 0.62 | 0.46 |
| Fucoxanthin | Navitoclax | 1 | 0-100 | 0.70 | 0.64 |

Conc, concentration; CI, Combination Index.

As seen in Table 2 and Table 3, a synergistic reduction of the IC50 was observed for combinations of fucoxanthin with Navitoclax (in both MV-4-11 and PL-21 cells), amarouciaxanthin A with Navitoclax and fucoxanthin with Venetoclax (in MV-4-11).

Example 2—Effects of Carotenoids and BCL2 Inhibitors in Senescence

Materials and Methods

Cell Cultures

Sk-Mel-103 cell line (human skin melanoma) was cultured in DMEM-high glucose supplemented with 10% FCS. All cells were cultured at 37° C. in a humidified 5% $CO_2$-atmosphere and were consistently free of mycoplasma, as evaluated by PCR. All passages were performed between 80 and 90% of confluence and with viability greater than 90%.

Treatment and Experimental Conditions $10^6$ Sk-Mel-103 cells were seeded in 24-well plates. Cultures were incubated with palbociclib (Palbo), as a senescence inductor; fucoxanthin; or a combination of them, as described in Table 4. After 7 days, cultures were treated with different concentrations of the BCL2 inhibitor Navitoclax. The cytotoxicity of each condition was determined through the calculation of IC50 (half maximal inhibitory concentration) by an MTT assay.

TABLE 4

Experimental conditions for the determination of the effects of fucoxanthin pretreatment on cells' sensibility to a BCL2 inhibitor.

| | Treatment at day 0 | | Treatment at day 7 |
|---|---|---|---|
| Condition | Paldociclib | Fucoxanthin | Navitoclax |
| Control cells | — | — | 0-100 μM |
| Senescent cells | 1 μM | — | 0-100 μM |
| Control cells + fucoxanthin | — | 4 μM | 0-100 μM |
| Senescent cells fucoxanthin | 1 μM | 4 μM | 0-100 μM |

MTT Assay

For cytotoxicity determination, cells were plated in 96-well microplates at a density of $10^4$ cells/well. After the initial treatments described above, different concentrations of Navitoclax were added. Plates were then incubated for 72 hours at 37° C. and 5% CO2. DMSO was used as vehicle control. After this period, 50 μL of SDS 10% were added to the negative control wells (0% viability, 100% mortality). Then, culture media was replaced by fresh media with 10 μL of MTT 5 mg/ml in PBS in each well. Plates were incubated for 4 hours at 37° C. and 5% CO2. Next, culture media was removed and 100 μL of extraction buffer (SDS, DSA, acetic acid 2%, pH 4.7) were added to each well. After incubating plates for 1 hour at 37° C. and 5% CO2, cultures were homogenized. Finally, plates were read at 570 nm with the spectrophotometer Multiskan Ascent (MTX Lab systems). The potency of each product was determined through the calculation of IC50 (half maximal inhibitory concentration).

Results

To study the effects of a pretreatment with fucoxanthin on cell sensibility to a BCL2 inhibitor, incubations palbociclib (senescence inductor) alone or in combination with fucoxanthin was performed for 7 days (as seen in Table 4). Afterwards, the cytotoxicity of Navitoclax (BCL2 inhibitor) was evaluated by MTT assay. Data was compared to control cells (non-senescent) in basal state or treated with fucoxanthin.

TABLE 5

IC50 of Navitoclax in Sk-Mel-103 cells treated with different conditions (6 replicates).

| | IC50 (μM) (mean ± SD) |
|---|---|
| Control cells | 8.017 ± 1.306 |
| Senescent cells | 0.136 ± 0.012 |

TABLE 5-continued

IC50 of Navitoclax in Sk-Mel-103 cells treated with different conditions (6 replicates).

| | IC50 (μM) (mean ± SD) |
|---|---|
| Control cells + fucoxanthin | 4.785 ± 0.911 |
| Senescent cells + fucoxanthin | 0.055 ± 0.005 |

SD, standard deviation.

As seen in Table 5, the IC50 of Navitoclax in control cells and senescent cells was reduced when cells were pretreated with fucoxanthin. Therefore, pretreatment with fucoxanthin increased the senolytic activity of Navitoclax.

Example 3—Effects of Carotenoids in Senescence

Materials and Methods

Cell Cultures

BJ-11 cell line (human primary skin fibroblasts) was cultured in MEM supplemented with 10% FCS plus 2 mM L-glutamine. All cells were cultured at 37° C. in a humidified 5% CO2-atmosphere and were consistently free of mycoplasma, as evaluated by PCR. All passages were performed between 80 and 90% of confluence and with viability greater than 90%.

Treatment and Experimental Conditions

In order to evaluate the effects of fucoxanthin on senescence, $10^4$ BJ-11 cells were seeded in 24-well plates. Cultures were incubated with different concentrations of palbociclib (Palbo) or doxorubicin (Doxo), as senescence inductors, and fucoxanthin (Fuco), as described in Table 6.

TABLE 6

Experimental conditions for the determination of fucoxanthin effects on senescence.

| | Senescence inductor | | Treatment |
|---|---|---|---|
| | Palbociclib | Doxorubicin | Fucoxanthin |
| Control cells (basal state) | — | — | — |
| Senescent cells | 1 μM | — | — |
| | — | 25 nM | — |
| Senescent cells + fucoxanthin | 1 μM | — | 10 μM |
| | — | 25 nM | 10 μM |

Doxorubicin treatments were performed only for 24 hours. After that, doxorubicin was removed and cells were cultured in complete culture medium during the periods of time indicated below. On the other hand, palbociclib was constantly present in the culture medium and added fresh periodically.

Two different approaches were followed:

Approach 1: Fucoxanthin Effects on Senescence Prevention

Cell cultures were simultaneously treated with fucoxanthin and the senescent inducers, as seen below. After 7 days, β-galactosidase activity was determined.

Figure 5A:
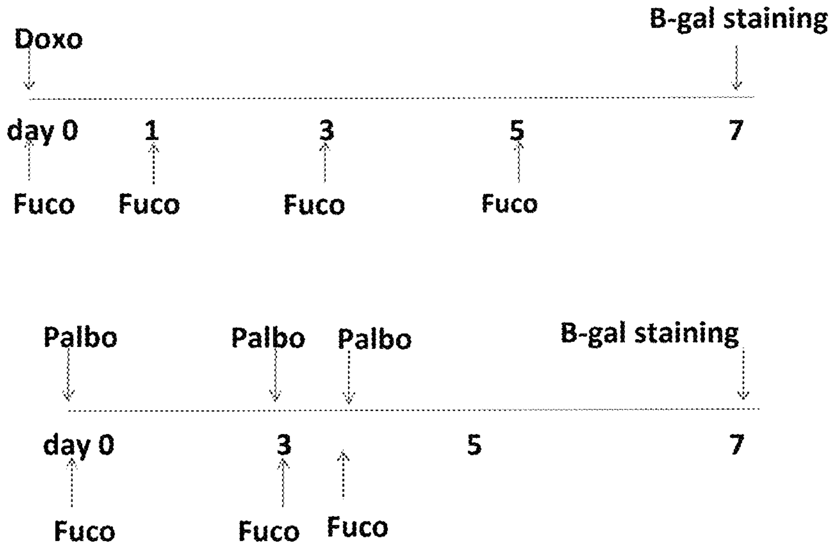
FIG. 5A depicts Scheme 1, which regards an experimental procedure to test fucoxanthin effects on senescence prevention.

FIG. 5A depicts Scheme 1, which regards an experimental procedure to test fucoxanthin effects on senescence prevention.

Approach 2: Fucoxanthin Effects on Senescence Reversion

Cell cultures were first treated with the senescent inducers for 7 days, as seen below. After that, treatment with fucoxanthin was performed for 7 days. At the end of this period β-galactosidase activity was determined.

Figure 5B:
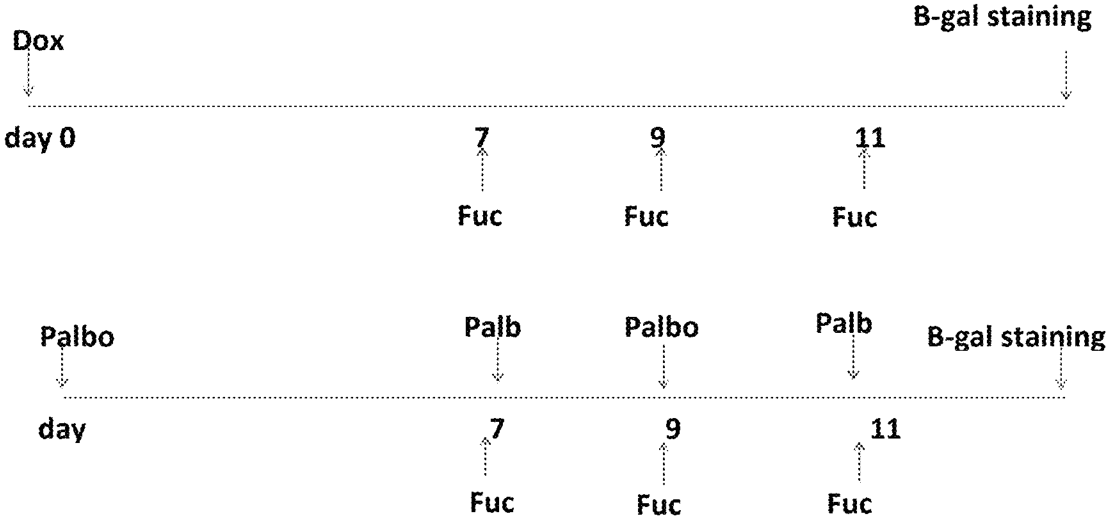
FIG. 5B depicts Scheme 2, which regards an experimental procedure to test fucoxanthin effects on senescence reversion.

FIG. 5B depicts Scheme 2, which regards an experimental procedure to test fucoxanthin effects on senescence reversion.

Senescence Associated 3-Galactosidase (SA-β-Gal) Staining

After treatments, SA-β-galactosidase staining was used for the determination of senescence-associated β-galactosidase expression in BJ-11 cells. β-galactosidase staining was performed based on manufacturer's recommendations (9860S, Cell Signaling Technology). Growth media was removed from the cells and the plate was rinsed once with PBS. Then, fixative solution was added to each well and cells were allowed to fix for 10-15 min at room temperature. The plate was rinsed twice with PBS before adding β-Galactosidase Staining Solution to each well. Finally, the plate was incubated at 37° C. for 24 h in a dry incubator (no $CO_2$) for preventing changes in pH, which may affect staining results. The amount of cells positive in β-galactosidase activity (stained in blue) was evaluated by manual stained-cell counting.

Results

To study fucoxanthin effects on the prevention and reversion of senescence, incubations with the cytostatic drugs doxorubicin and palbociclib were performed in BJ-11 cells as previously described. β-galactosidase activity was determined and used as senescence marker. The percentage of senescent cells positive in β-galactosidase activity was reduced after fucoxanthin treatment as seen in Table 7 and Table 8.

TABLE 7

Percentage of cells positive in β-galactosidase activity in Approach 1 (evaluation of fucoxanthin effects on senescence prevention).

| | Palbociclib | Doxorubicin |
|---|---|---|
| Control cells (basal state) | 0% | 0% |
| Senescent cells | >98% | >80% |
| Senescent cells + fucoxanthin | <5% | <5% |

TABLE 8

Percentage of cells positive in β-galactosidase activity in Approach 2 (evaluation of fucoxanthin effects on senescence reversion).

| | Palbociclib | Doxorubicin |
|---|---|---|
| Control cells (basal state) | <2% | <2% |
| Senescent cells | >95% | >80% |
| Senescent cells + fucoxanthin | <5% | <5% |

Example 4—Effects of Carotenoids in the Reduction of Senescence-Associated Secretory Phenotype (SASP)

Materials and Methods

Cell Cultures

Sk-Mel-103 cell line (human skin melanoma) was cultured in DMEM-high glucose supplemented with 10% FCS. All cells were cultured at 37° C. in a humidified 5% CO2-atmosphere and were consistently free of mycoplasma, as evaluated by PCR. All passages were performed between 80 and 90% of confluence and with viability greater than 90%.

Treatment and Experimental Conditions $10^6$ Sk-Mel-103 cells were seeded in 24-well plates. Cultures were incubated with palbociclib or doxorubicin, as senescence inductors; fucoxanthin; or a combination of them, as described in Table 9. After treatments, cells and supernatants were collected by centrifugation and stored at −20° C.

TABLE 9

Experimental conditions for the determination of fucoxanthin effect on SASP

| | Palbociclib | Doxorubicin | Fucoxanthin |
|---|---|---|---|
| Senescent cells | 1 μM | — | — |
| | — | 125 nM | — |
| Senescent cells + fucoxanthin | 1 μM | — | 4 μM |
| | — | 125 nM | 4 μM |

Determination of Secreted Interleukins (ILs)

Secretion of IL-1β, IL-6 and IL-8 was quantified in the supernatants by commercial ELISA kits (DY201, DY206, DY208, R&D Systems) following manufacturer's instructions. Obtained values were normalized by total cell protein content in each well at the end of the experiment, quantified by Bradford assay (B6916, Sigma-Aldrich). A second normalization was performed by dividing the secreted interleukin after fucoxanthin incubations by its corresponding control of senescent cells.

Results

IL-1β, IL-6 and IL-8 are upregulated in senescent cells and constitute part of the SASP. To study fucoxanthin effects on SASP factors, secreted ILs were quantified in the supernatants of SK-Mel-103 cells, where senescence was induced with doxorubicin or palbociclib.

Figure 2:
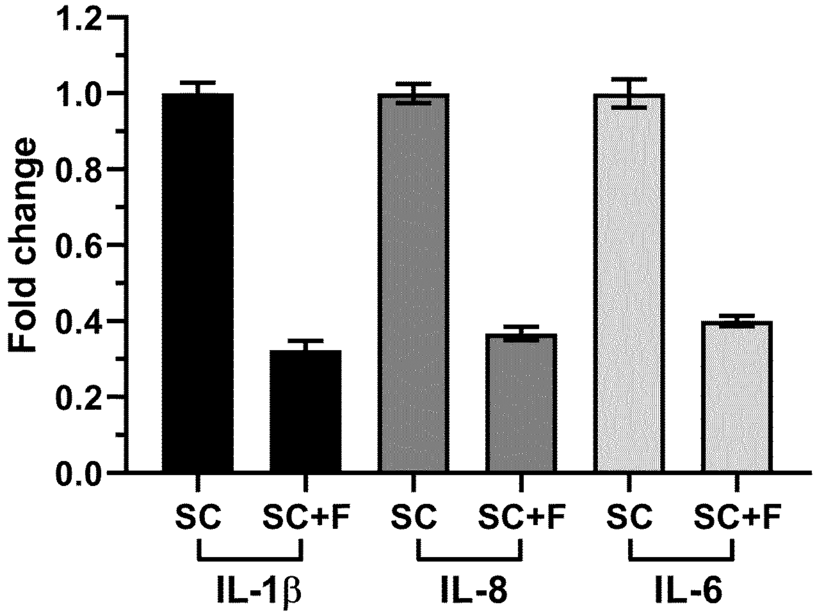
FIG. 2. ILs secretion by SK-Mel-103 cells upon treatment with doxorubicin. Error bars indicate the standard deviation from 3 technical replicates. SC, senescent cells; F, fucoxanthin.

As shown in FIG. 1 and FIG. 2, the secretion of IL-1β, IL-6 and IL-8 was significantly decreased upon incubations with fucoxanthin for both pro-senescent treatments (p value<0.01).

Example 5—Effects of Amarouciaxanthin a on Liver Fibrosis

Hepatic stellate cells (HSC) are found in the perisinusoidal space of the liver. They constitute the major cell type involved in liver fibrosis, being responsible for the formation of scar tissue in response to liver damage.

Materials and Methods

Experimental Conditions

To evaluate the effect of amarouciaxanthin A on HSC activation, the immortalized human cell line LX2 was used.

Additionally, primary HSC were extracted from cirrhotic rats which had been subjected to carbon tetrachloride inhalation. In both cases, cells were cultured for 24 h before adding the compound. After that, either amarouciaxanthin A at 10 μM or the vehicle (DMSO) was added to the culture. Cells were harvested at 24 and 72 h post treatment and were lysed to analyze fibrotic biomarkers. Gene transcription was determined by quantitative PCR at 24 and 72 h and protein expression by western blotting at 72 h. α-smooth muscle actin (α-SMA) was analyzed in rat HSC. Collagen I a1 (COL1A1), which is the main component of the extracellular matrix, was analyzed in LX2.

Results

α-SMA is a structural protein that forms microfilaments and a common activation biomarker for HSC. HSC increase the synthesis of COL1A1 under pathologic conditions, contributing to the apparition of hepatic fibrosis.

Figure 3:
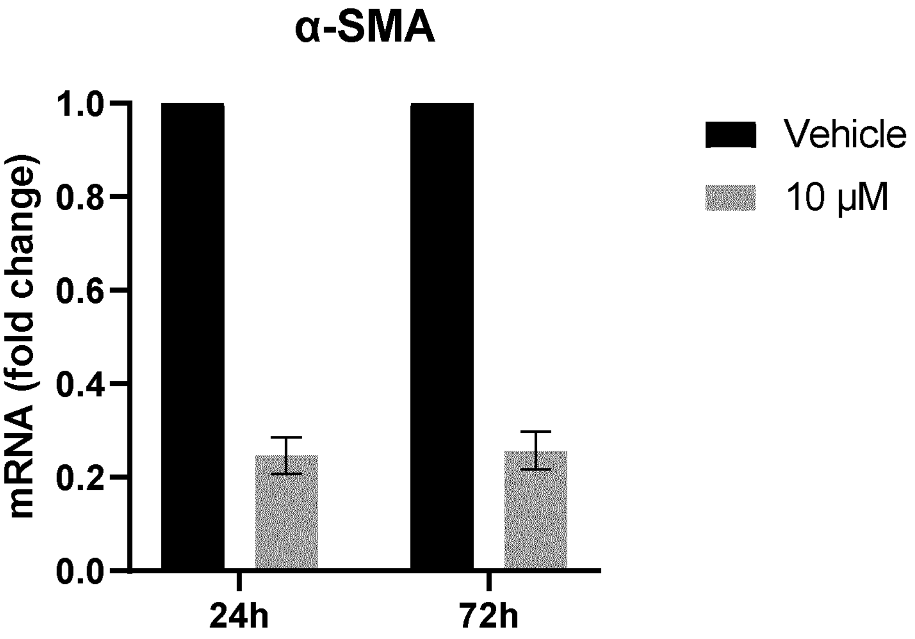
FIG. 3. Fold change in α-SMA expression in HSC from cirrhotic rats when incubated with 10 μM of amarouciaxanthin A. Values are normalized to vehicle control and error bars indicate standard deviation.
Figure 3:
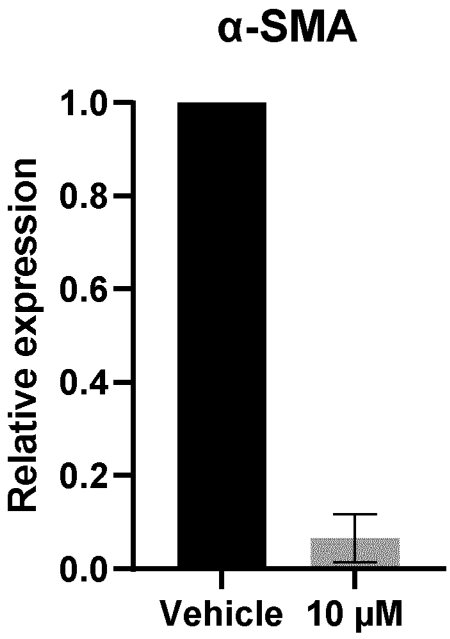
Figure 4:
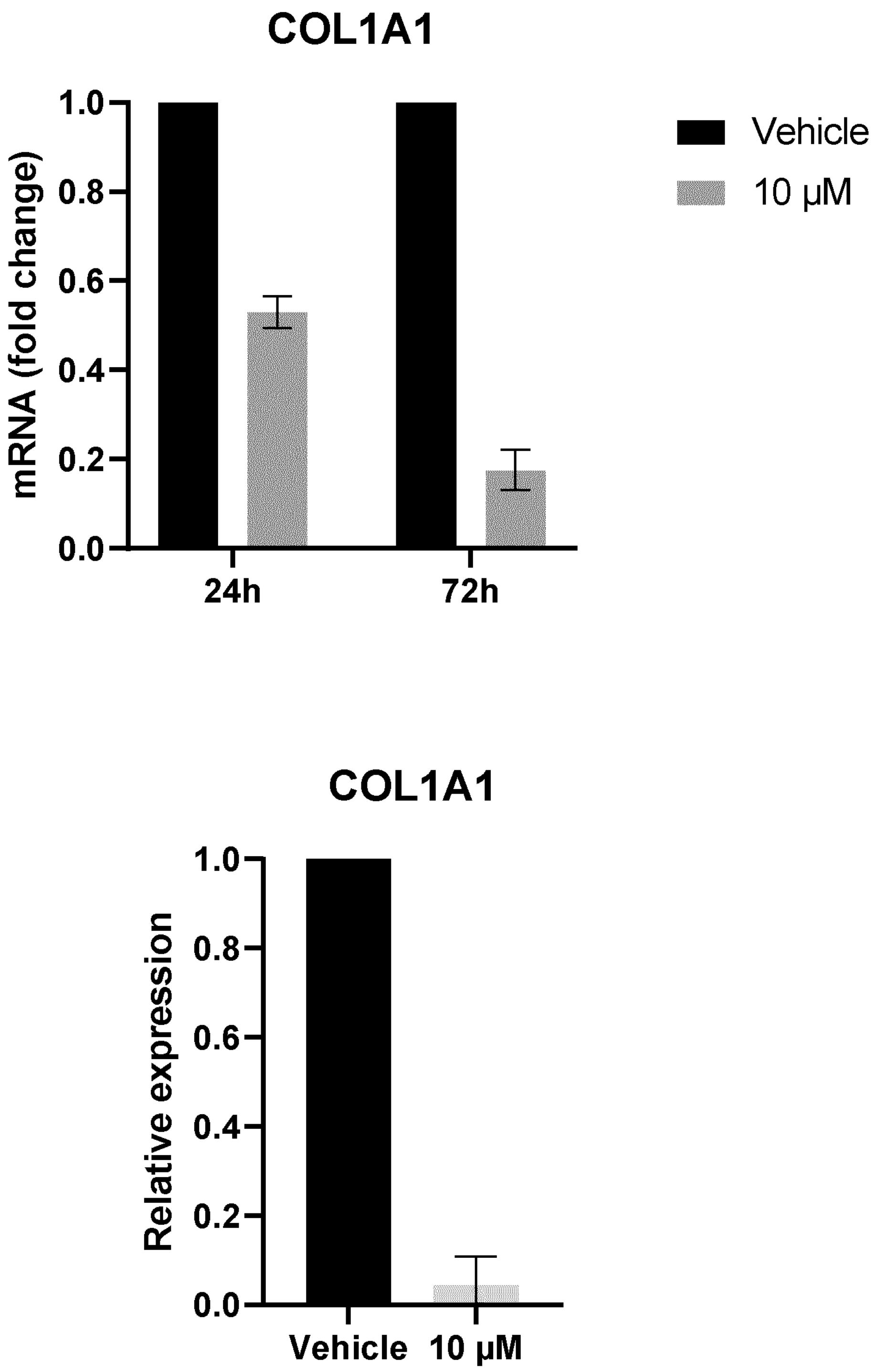
FIG. 4. Fold change in COL1A1 expression in LX2 cells when incubated with 10 μM of amarouciaxanthin A. Values are normalized to vehicle control and error bars indicate standard deviation.

As shown in FIG. 3, amarouciaxanthin A inhibited α-SMA transcription in cirrhotic rat HSC by around 80% after 24 h and 72 h. Expression at the protein level was also diminished by 95%. The xanthophyll also inhibited COL1A1 transcription in human LX2 cells by around 50% after 24 h and 80% after 72 h (FIG. 4). Collagen expression was reduced around 95% as quantified by western blot (FIG. 4).

In conclusion, amarouciaxanthin A promotes HSC inactivation and inhibits the exacerbated synthesis of extracellular matrix, as proved by the downregulation of the fibrotic markers both at the transcriptional and translational levels.

The invention claimed is:

1. A combination comprising amarouciaxanthin A and venetoclax or amarouciaxanthin A and navitoclax.

2. The combination of claim 1 having a form chosen from the group consisting of a cosmeceutical, a nutraceutical, a cosmetic and a pharmaceutical composition.

3. A method for treating acute myelogenous leukemia (AML) comprising administering the combination according to claim 2 to a subject in need thereof.

4. The method according to claim 3, wherein the subject is a human.

5. A method for treating skin cancer or a hematologic cancer comprising administering the combination according to claim 2 to a subject in need thereof, wherein the combination has the form that is the pharmaceutical composition.

6. The method according to claim 5, wherein the hematologic cancer is selected from the group consisting of acute myelogenous leukemia (AML), non-Hodgkin's lymphomas (NHL), myelodysplastic syndromes (MDS), multiple myeloma (MM), Chronic lymphocytic leukemia (CLL), and myelofibrosis, and the skin cancer is melanoma.

7. A method for treating acute myelogenous leukemia (AML) comprising administering the combination according to claim 1 to a subject in need thereof.

8. The method according to claim 7, wherein the subject is a human.

* * * * *